US008491658B1

(12) United States Patent
Etminan

(10) Patent No.: US 8,491,658 B1
(45) Date of Patent: Jul. 23, 2013

(54) INTERBODY FUSION IMPLANT AND RELATED METHODS

(76) Inventor: Mohammad Etminan, Houston, TX (US)

( * ) Notice: Subject to any disclaimer, the term of this patent is extended or adjusted under 35 U.S.C. 154(b) by 29 days.

(21) Appl. No.: 12/834,855

(22) Filed: Jul. 12, 2010

Related U.S. Application Data

(60) Provisional application No. 61/224,887, filed on Jul. 12, 2009.

(51) Int. Cl.
*A61F 2/44* (2006.01)

(52) U.S. Cl.
USPC ...................................................... 623/17.16

(58) Field of Classification Search
CPC ..................................................... A61F 2/447
USPC .......................................... 623/17.11–17.16
See application file for complete search history.

(56) References Cited

U.S. PATENT DOCUMENTS

| 7,018,416 B2 | 3/2006 | Hanson et al. | 623/17.16 |
| 7,232,463 B2 | 6/2007 | Falahee | 623/17.11 |
| 2004/0034430 A1 | 2/2004 | Falahee | 623/17.16 |
| 2005/0143819 A1 | 6/2005 | Falahee | 623/17.11 |
| 2007/0093898 A1 | 4/2007 | Schwab et al. | 623/17.11 |
| 2009/0030519 A1* | 1/2009 | Falahee | 623/17.16 |

OTHER PUBLICATIONS

"Extreme Laternal Interbody. Fusion, XLIF, Minimally Invasive Brain and Spine Surgery" <http://ccmibs.com/xlif.minimally-invasive-spine-surgery-fremont-ca.html> (accessed Jul. 6, 2012).

\* cited by examiner

*Primary Examiner* — Ellen C Hammond
(74) *Attorney, Agent, or Firm* — Ostrolenk Faber LLP

(57) ABSTRACT

An implant for performing interbody fusion within a human spine, inserters for such an implant, and associated methodology. The implant is preferably formed in situ from at least two separate but lockable members (a base member and a closure member). The base member may be implanted into an interbody space first, after which the end plates may be finally prepared and the base member packed with fusion promoting substances before engaging and locking the closure member. The closure member provides structural support for the adjacent vertebral bodies (along with the base member) and may be selected after implantation of the base member having a specific length, width, height, taper, etc. . . . to ensure an optimal sizing of the implant for desired restoration of disc height, coronal taper, sagittal taper, etc. . . . .

9 Claims, 28 Drawing Sheets

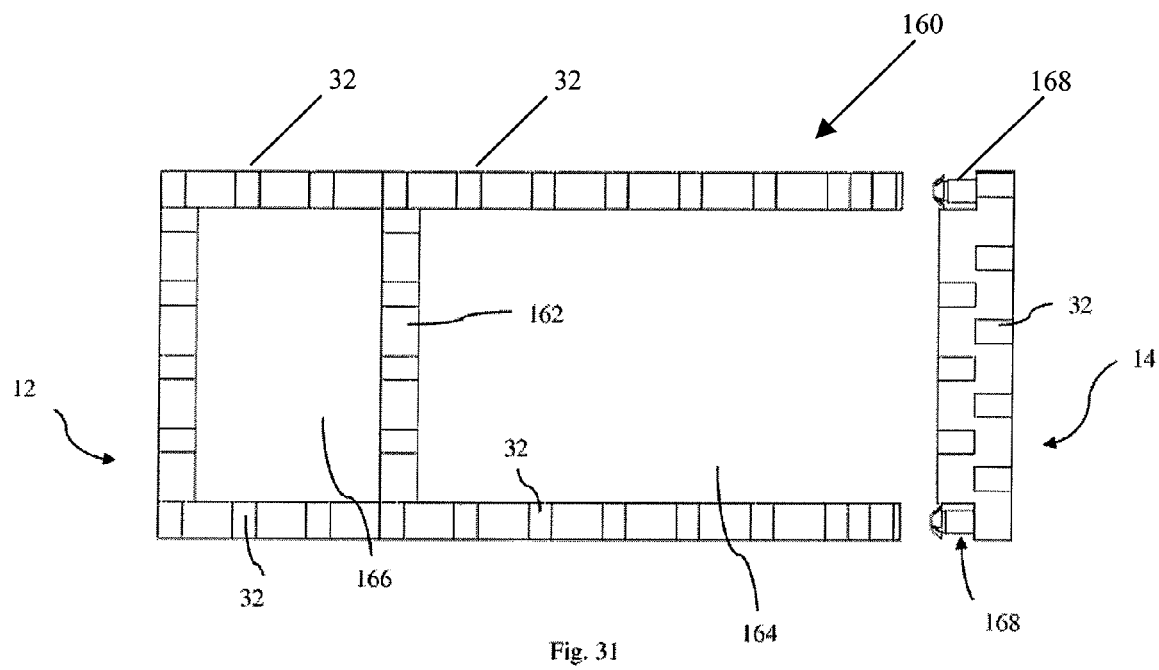
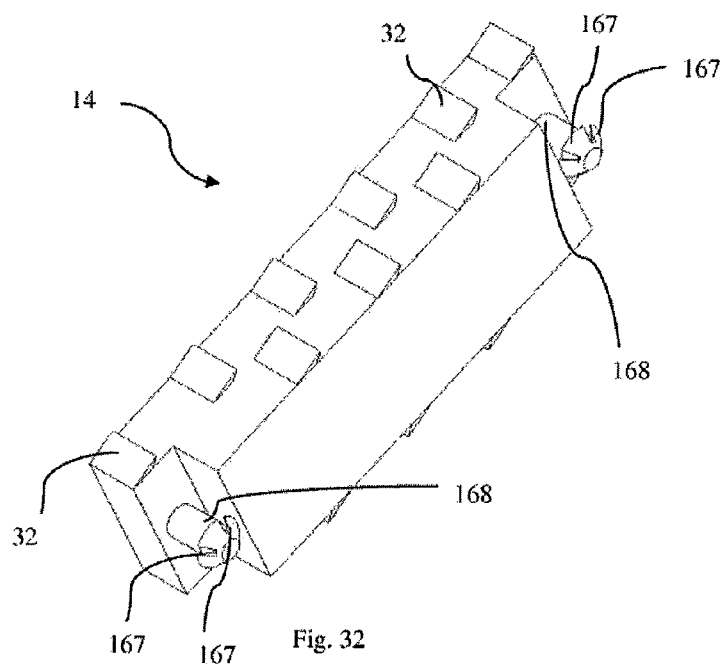
Fig. 31
Fig. 32

INTERBODY FUSION IMPLANT AND RELATED METHODS

CROSS REFERENCE TO RELATED APPLICATIONS

The present application is a non-provisional patent application claiming the benefit of priority under 35 U.S.C. §119 (e) from U.S. Provisional Application No. 61/224,887 filed on Jul. 12, 2009, the entire contents of which are hereby expressly incorporated by reference into this disclosure as if set forth fully herein.

BACKGROUND OF THE INVENTION

1. Field of Invention

The present invention relates to an implant for performing interbody fusion within a human spine, inserters for such an implant, and associated methodology. More specifically, the implant aspect of the present invention involves an implant formed in situ from at least two separate but lockable members (a base member and a closure member), wherein: (a) the base member may be implanted into an interbody space first, after which the end plates may be finally prepared and the base member packed with fusion promoting substances before engaging and locking the closure member; and (b) the closure member provides structural support for the adjacent vertebral bodies (along with the base member) and may be selected after implantation of the base member having a specific length, width, height, taper, etc. . . . to ensure an optimal sizing of the implant for desired restoration of disc height, coronal taper, sagittal taper, etc. . . . .

2. Discussion of the Prior Art

The human spinal column is made up of a series of vertebral bodies with intervertebral discs disposed there between, which collectively provide support and structure for the body while allowing motion and flexibility, as well as protection for the spinal cord running through the spinal column and associated nerve roots which exit the spinal column. Various traumatic events and/or degenerative conditions may result in undesirable motion or change in disc height, both of which may cause chronic pain for the affected individual. The degree and treatment of pain varies by the individual but in many instances the pain can be disabling and uncontrollable by conservative means, leaving surgery as the only viable option. In many cases, the primary surgical treatment involves interbody fusion, wherein an implant is introduced into the disc space to restore the disc height and establish a bony bridge between the adjacent vertebral bodies with the goal of eliminating or at least reducing the pain of the affected individual.

To enable the introduction of an interbody fusion implant, the surgeon must perform the following steps to create a suitable environment for post-operative fusion: (a) surgical access to the affected disc space; (b) an annulotomy to gain access into the interior of the affected disc; (c) an initial or preliminary discectomy to remove some or all of the nucleus pulposus within the affected disc; and (d) final endplate preparation to remove the cartilaginous disc material to expose the underlying bony endplates of the adjacent vertebral bodies (preferably without violating the bony endplates). Final endplate preparation is a critical step in implant placement and achieving a solid fusion. It is required to remove all the cartilaginous disc material while not violating the bony end plate. Not removing the cartilaginous end plate can result in a delayed bony growth or incomplete bony growth, while fracturing the bony end plate can result in a fracture of the vertebral body and post-operative settling of the implant with concomitant loss of disc height and/or vertebral body alignment. Repetitive insertion of instruments into the disc space during the process of final endplate preparation can result in possible injury to the neural and vascular structures surrounding the disc space if the instruments are inadvertently passed or extended outside the disc space by the surgeon.

To help facilitate fusion, the implants preferably include one or more "fusion windows," that is, apertures extending from the superior surface to the inferior surface of the implant to allow bone to form through the implant to ensure a solid and robust fusion. To further facilitate fusion, these apertures may be filled with fusion promoting materials including but not limited to cancellous autograft bone, allograft bone, demineralized bone matrix (DBM), porous synthetic bone graft substitute, bone morphogenic protein (BMP), mesenchymal stem cells and/or combinations thereof and/or functional equivalents. Such materials are traditionally introduced into the implant before the implant is introduction into the disc space. Based on the oftentimes high amount of force required to be applied to the corresponding insertion tools, such fusion promoting substances can become loosened or dislodged during the introduction of the implant, which can in certain instances increase the amount of time required to achieve fusion.

Implants can be introduced into the interbody space in one of several known approaches or directions to the spine, including posterior (from the back), anterior (from the front), and lateral (from the side). Before 2003, interbody fusion via a lateral approach was uncommon because of the inability to safely pass through the psoas muscle, which flanks either side of the lumbar spine and includes the lumbar plexus. Lateral access surgery became safe and reproducible with the advent of the NeuroVision® system by NuVasive, Inc., which automatically detects the presence of nerves in the psoas muscle via surgeon-directed neurophysiology in combination with minimally disruptive access instrumentation (e.g. dilators, retractor, etc. . . . ) to aid the surgeon in avoiding nerves while establishing an operative corridor from a lateral approach.

The present invention addresses the need for additional interbody implant options, inserters, and techniques for use in lateral access surgery.

SUMMARY OF THE INVENTION

The present invention involves a novel interbody fusion implant for use in lateral access surgery, inserters for said implant, and associated methodology. The interbody fusion implant has two separate but lockable members (a base member and a closure member). According to an aspect of the present invention, the base member and closure member are complimentary to each other so that they can be engaged and thereafter locked together while in a lumbar or thoracic interbody space. The base member is configured in a generally elongated U-shaped manner with generally parallel side walls coupled to an end wall positioned generally perpendicularly with the side walls. The base member and closure member may be equipped with any number of suitable locking features to lock the closure member to the base member.

According to an aspect of the present invention, the base member is introduced into the interbody space before the closure member. By doing so, and given the U-shaped configuration of the base member, this allows for an aggressive final end plate preparation, inspection of the final position of base member within the disc space, and packing of fusion promoting material after the base member is implanted but before the closure member is implanted. This presents a host of benefits, which will be described in detail below, along with the specific method steps associated with the use of the base member and closure member during lateral access surgery according to an aspect of the present invention. The introduction of the base member is facilitated through the use of a specialized inserter designed to bolster the structural integrity of the base member during insertion to reduce the likelihood of having the base member fracture under the impaction forces typically involved in interbody fusion procedures. The introduction of the base member is also facilitated via the tapered leading end, which serves as a general wedge between the adjacent vertebral bodies during insertion of the base member into the disc space during impaction.

After the fusion promoting material is introduced into the base member, the closure member can be engaged and locked to the base member according to an aspect of the present invention. In general, however, this manner of constructing the implant in situ within the interbody space offers a host of additional features beyond those of traditional interbody implants of unibody construction. It offers an enhanced safety profile based on the protection offered by the base member during final endplate preparation, which forms a barrier such that the associated instruments for final endplate preparation cannot be inadvertently passed or extended outside the disc space by the surgeon and into contact with the adjacent neural and vascular structures. It offers increased efficiency in final endplate preparation by limiting the area of final endplate preparation to just that area within the interior of the base member. It also advantageously separates the weight bearing portion of the base member (i.e. the upper and lower contact surfaces) from the potential fusion area created within the interior of the base member, thereby allowing for an aggressive removal of the cartilaginous endplates within interior of the base member (e.g. extending into the cancellous bone to cause ample bleeding to promote the fusion process).

In situ formation of the implant of the present invention also prevents or reduces the risk of subsidence of the implant into the softer cancellous bone in two distinct manners. First, it does so by not requiring the cartilaginous endplates to be removed prior to implant introduction as is required with traditional implants. In other words, this allows the cartilaginous endplates to provide protection against fracturing the underlying vertebral body during the introduction of the base member, which can occur during the implantation of traditional interbody implants of unibody construction if the surgeon is not careful to avoid. It also prevents or reduces subsidence by allowing the length of the closure member to be selected after the implantation of the base member to maximize the surface area of the overall implant to ensure leading and trailing ends of the result implant are positioned on the stronger cortical bone forming the ring apophysis around the periphery of the vertebral bodies. In this regard, both the base member and the closure member are in direct contact with upper and lower vertebral bodies, thereby bearing weight and sharing the associated loads. The height of the closure member can also be determined after the implantation of the base member and may be different from the height of the base member, allowing for possible correction of a coronal deformity in the interbody space.

Finally, in situ implant formation also advantageously allows a surgeon to aggressively pack the fusion promoting material into the implant more than may be capable with conventional implants of unibody construction. This is because the surgeon need only pack the fusion promoting material into the base member after implantation, as opposed to impacting an implant that has been packed with fusion promoting material before implantation and dislodge or loosen the fusion promoting material as is the case with traditional implants.

BRIEF DESCRIPTION OF THE DRAWINGS

FIG. 31 is a top exploded view of the interbody fusion implant of FIG. 30 according to an aspect of the present invention;

FIG. 32 is a perspective view of the closure member of FIG. 30 according to an aspect of the present invention;

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The interbody implant, inserters, and associated methodology for spinal fusion using a lateral approach to the spine disclosed herein boasts a variety of inventive features and components that warrant patent protection, both individually and in combination.

Figure 1:
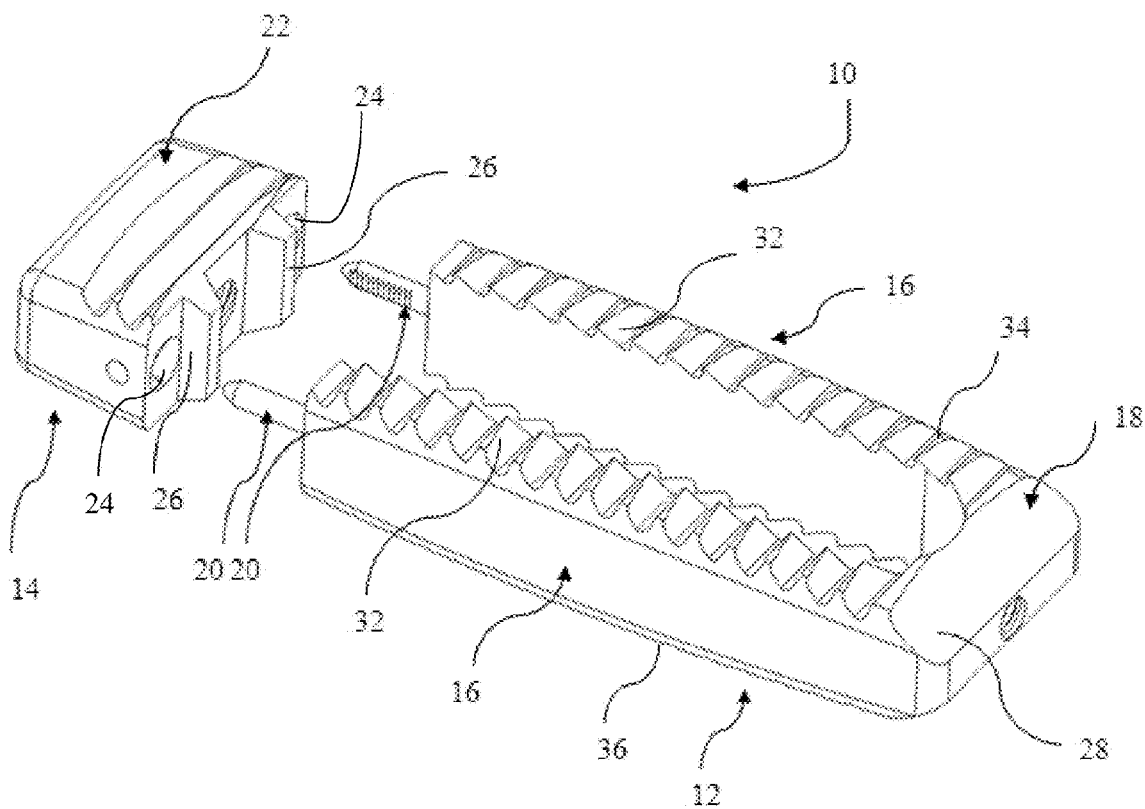
FIG. 1 is a perspective exploded view of an interbody fusion implant including a base member and a closure member according to an aspect of the present invention.

FIG. 1 is a perspective exploded view of an interbody fusion implant 10 including a base member 12 and a closure member 14 according to an aspect of the present invention. The base member 12 and closure member 14 are complimentary to each other so that they can be engaged and thereafter locked together while in a lumbar or thoracic intervertebral (aka interbody) space. The base member 12 is configured in a generally elongated U-shaped manner with generally parallel side walls 16 coupled to an end wall 18 positioned generally perpendicularly with the side walls 16. The base member 12 includes, by way of example only, locking features in the form of locking pins 20 extending longitudinally away from the trailing ends of the side walls 16. The closure member 14 includes a main body 22 with complimentary locking features in the form of recesses 24 to receive the locking pins 20 of the base member 12 and extensions 26 extending generally longitudinally away from the main body 22 towards the base member 12. The mechanics and operation of this exemplary locking mechanism will be described in greater detail below.

Figure 2:
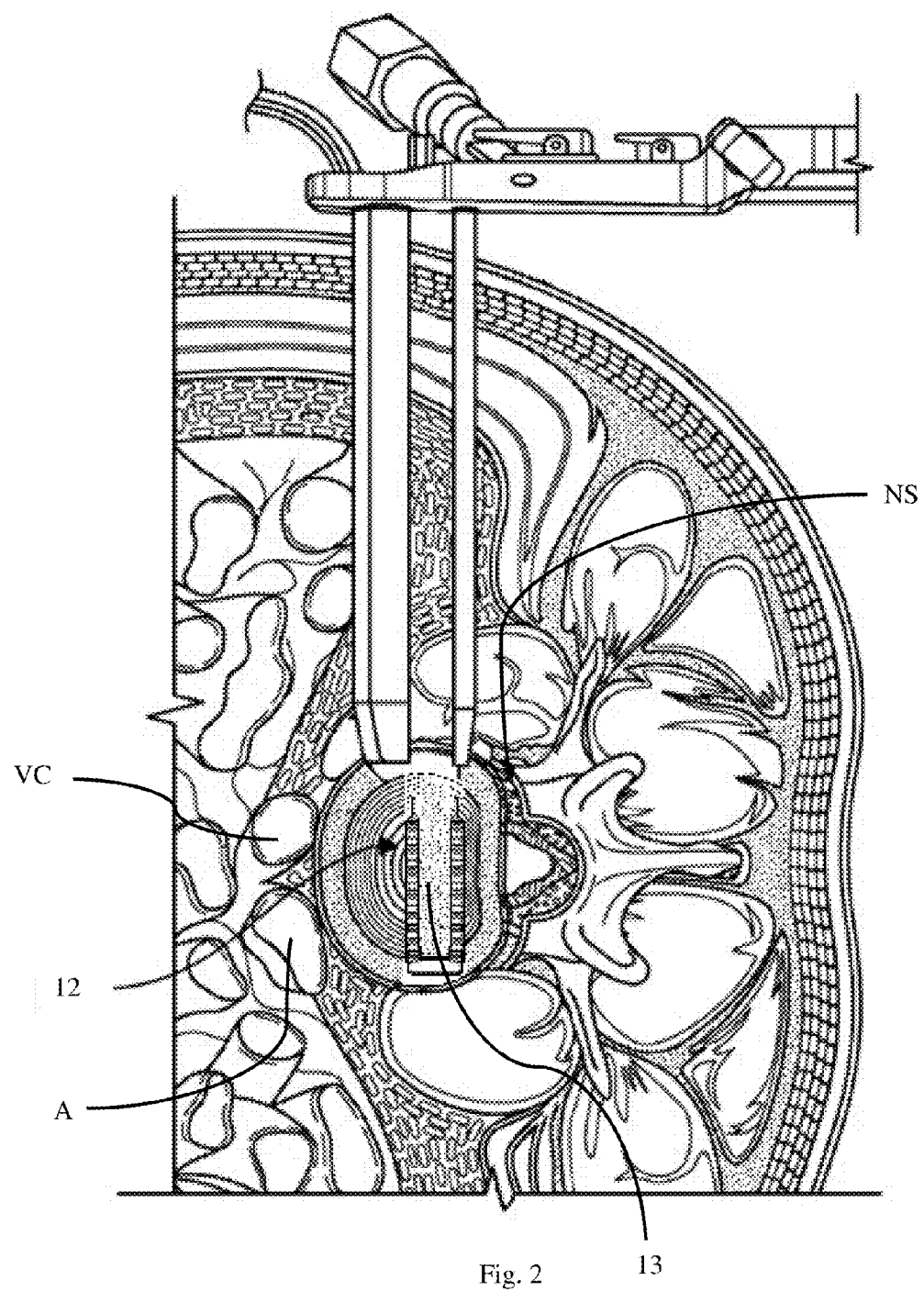
FIG. 2 is a cross sectional view of a patient during lateral access surgery with the base member of FIG. 1 in the interbody space (with final endplate preparation having been performed after the implantation of the base member) according to aspects of the present invention.
Figure 3:
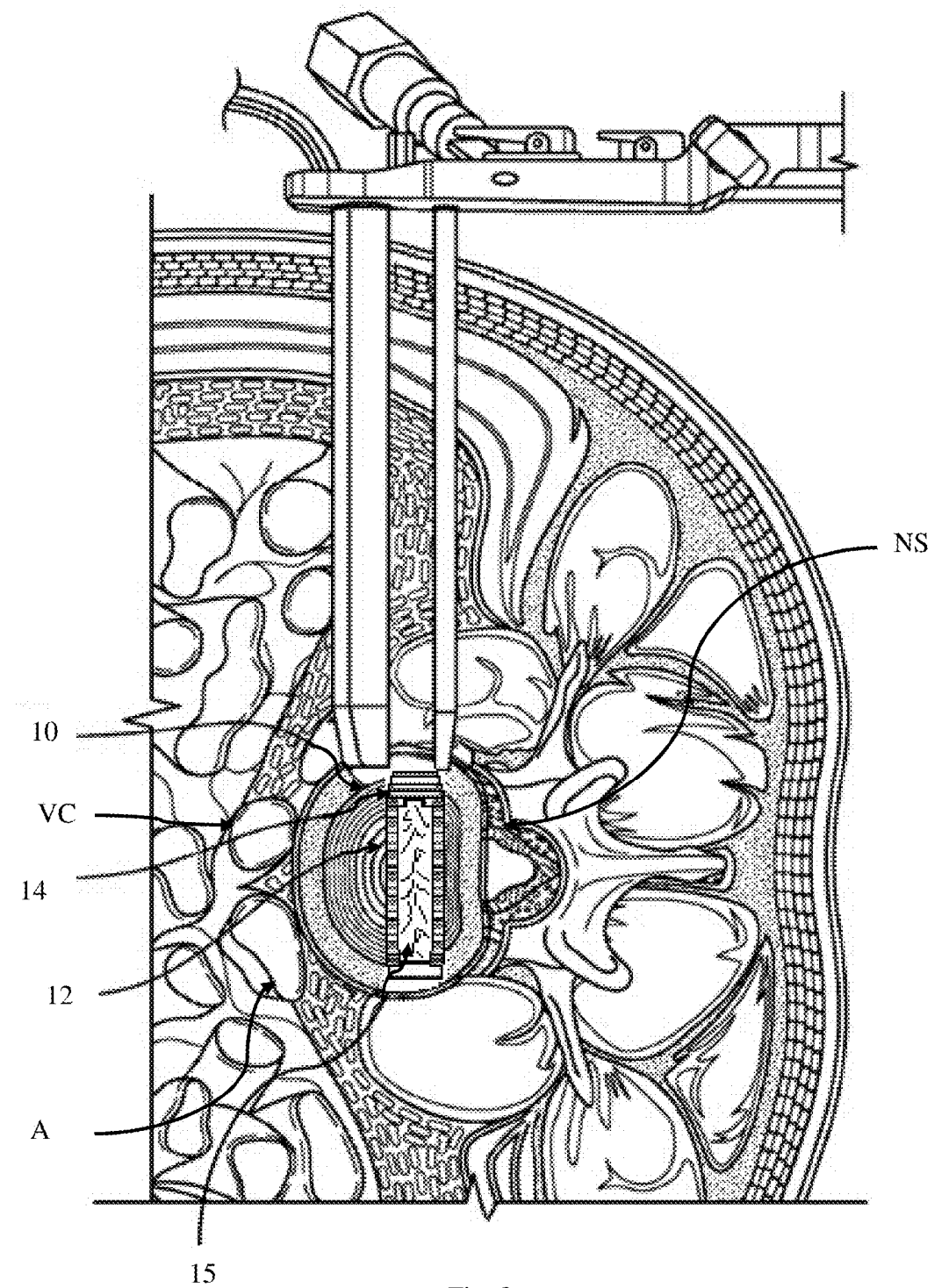
FIG. 3 is a cross sectional view of a patient during lateral access surgery with the closure member of FIG. 1 attached to the base member of FIG. 1 (with fusion promoting material disposed therein, having been introduced after the implantation of the base member but before the implantation of the closure member) according to aspects of the present invention.

With reference to FIGS. 2 and 3, according to an aspect of the present invention, the base member 12 is introduced into the interbody space before the closure member 14. By doing so, and given the U-shaped configuration of the base member 12, this allows for inspection of the base member 12 to ensure optimal positioning before final endplate preparation, an aggressive final vertebral end plate preparation to create a fully prepared fusion area 13 with the base member 12, and packing of fusion promoting material 15 into the fusion area 13 after the base member 12 has been implanted but before the closure member 14 is implanted (FIG. 2). This presents a host of benefits, which will be described in detail below, along with the specific method steps associated with the use of the base member 12 and closure member 14 during lateral access surgery according to an aspect of the present invention. The introduction of the base member 12 is facilitated through the use of a specialized inserter (not shown, but described below) designed to bolster the structural integrity of the base member 12 during insertion to reduce the likelihood of having the base member 12 fracture under the impaction forces typically involved in interbody fusion cases. The introduction of the base member 12 is also facilitated via the slightly tapered leading end 28, which serves as a general wedge between the adjacent vertebral bodies during insertion of the base member 12 into the disc space during impaction.

After the fusion promoting material is introduced into the base member 12, the closure member 14 can be engaged and locked to the base member 12 as shown generally in FIG. 3 and as will be described in greater detail below. In general, however, this manner of constructing implant 10 in situ within the interbody space is advantageous in that it allows a surgeon to aggressively and efficiently prepare the bony endplates that will serve for a fusion bed within the base member 12 while the sides of the base member 16, and 18 protect the surrounding neurovascular structures (such as the vena cava VC, aorta A and posterior neural structures NS) as well as the weight bearing portions of the vertebral end plates. The design also allows the surgeon to aggressively pack fusion promoting material into the implant 10 more than may be capable with conventional, unitary designs. In addition, the length of the closure member 14 may be selected after the implantation of the based member 12 to maximize the surface area of the over implant 10 to ensure the leading and trailing ends of the implant 10 are positioned on the stronger cortical ring apophysis of the vertebral bodies, thereby minimizing the risk of subsidence into the softer cancellous region. In this regard, both the base member 12 and the closure member 14 are in direct contact with upper and lower vertebral end plates, thereby bearing weight and sharing the loads from the end plates. The height of the closure member 14 can also be determined after the implantation of the base member 12 (differing from the height and/or curvature of the base member 12) allowing for possible of correction of coronal deformity within the disc space or adjacent vertebral bodies.

Figure 4:
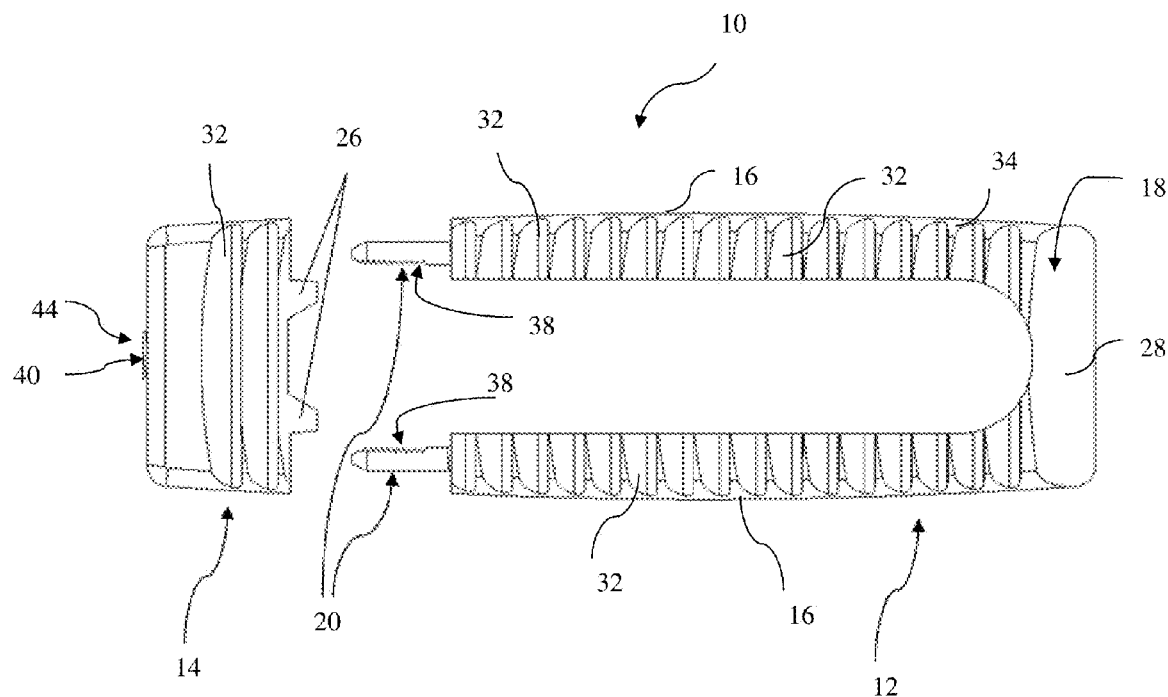
FIG. 4 is a top exploded view of the interbody fusion implant of FIG. 1 according to an aspect of the present invention.
Figure 5:
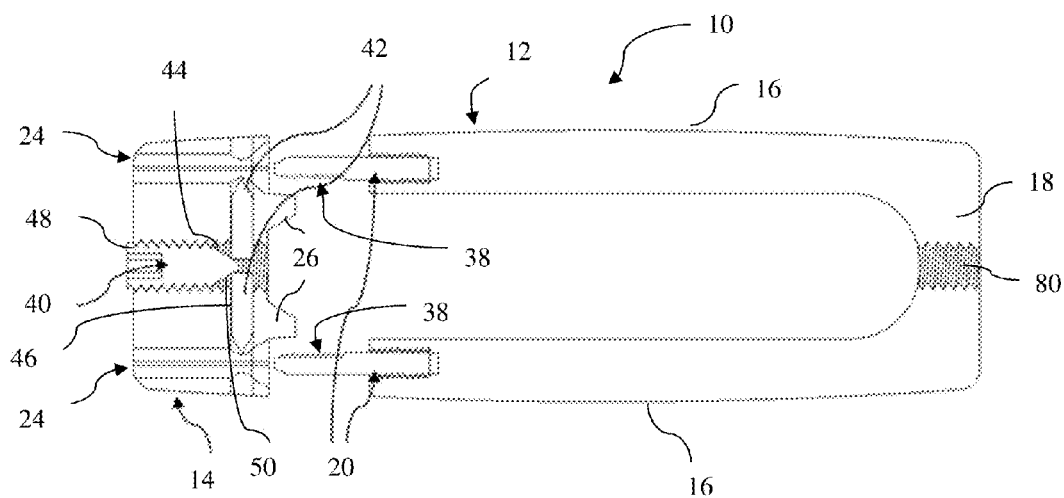
FIG. 5 is a top exploded view, in partial cross section, of the interbody fusion implant of FIG. 1 illustrating the locking features between the base and closure members before engagement and locking of the closure member to the base member according to an aspect of the present invention.

With reference to FIGS. 4-5, by way of example only, according to an aspect of the present invention the base member 12 includes locking pins 20 and the closure member 14 includes recesses 24. The closure member 14 has two tabs 26 extending outward in the opposite direction of the recesses 24. The tabs 26 align the closure member 14 with the base member 12 when the closure member 14 is being attached to the base member 12 in the interbody space. Both the base member 12 and the closure member 14 include a series of anti-migration features 32 on the upper and lower surfaces 34, 36 to help prevent migration of the implant relative to the adjacent vertebral bodies while in the interbody space. Although shown as angled teeth, the anti-migration features 32 may be configured and arranged in any number of suitable manners and structures sufficient to prevent or minimize the propensity for the implant 10 to migrate or move after implantation.

As shown in FIG. 5, the locking pins 20 of the base member 12 are (by way of example only) separate components that are affixed to the base member 12 prior to the installation of the base member 12 into the interbody space. By using separate pieces for the locking pins 20, the locking pins 20 can be of the same or different material than that of the base member 12. In one aspect, the locking pins 20 may be of a metallic construction to simultaneously serve as radiopaque markers to aid in the visualization of the base member 12 or implant 10 during and/or after implantation, particularly when the base member 12 and closure member 14 are constructed of radiolucent material, such as poly-ether-ether-ketone (PEEK) and/or other suitable biocompatible and radiolucent materials. Although shown as separate components in FIG. 5, the base member 12 and locking pins 20 may be constructed in a unitary fashion without departing from the scope of the invention. Similarly, the locking features shown and described with reference to FIG. 5 could be reversed, with the locking pins 20 extending from the closure member 14 and the tabs 26 extending from the base member 12, without departing from the scope of the invention.

In either event, the recesses 24 of the closure member 14 are preferably complimentary to the shape of the locking pins 20 of the base member 12 to facilitate the engagement of the closure member 14 to the base member 12 during use. Depending upon the tolerance between the recesses 24 and the locking pins 20, the sheer act of advancing the locking pins 20 within the recesses 24 may serve as the primary (and possibly only) manner of locking the closure member 14 to the base member 12 via a resulting friction fit. To facilitate this, locking pins 20 may include a variety of serrations 38 to help engage the interior of the recesses 24. If desired, the recesses 24 and locking pins 20 may be dimensioned to allow for some clearance between the serrations 38 of the locking pins 20 and the interior of the recesses 24.

Figure 6:
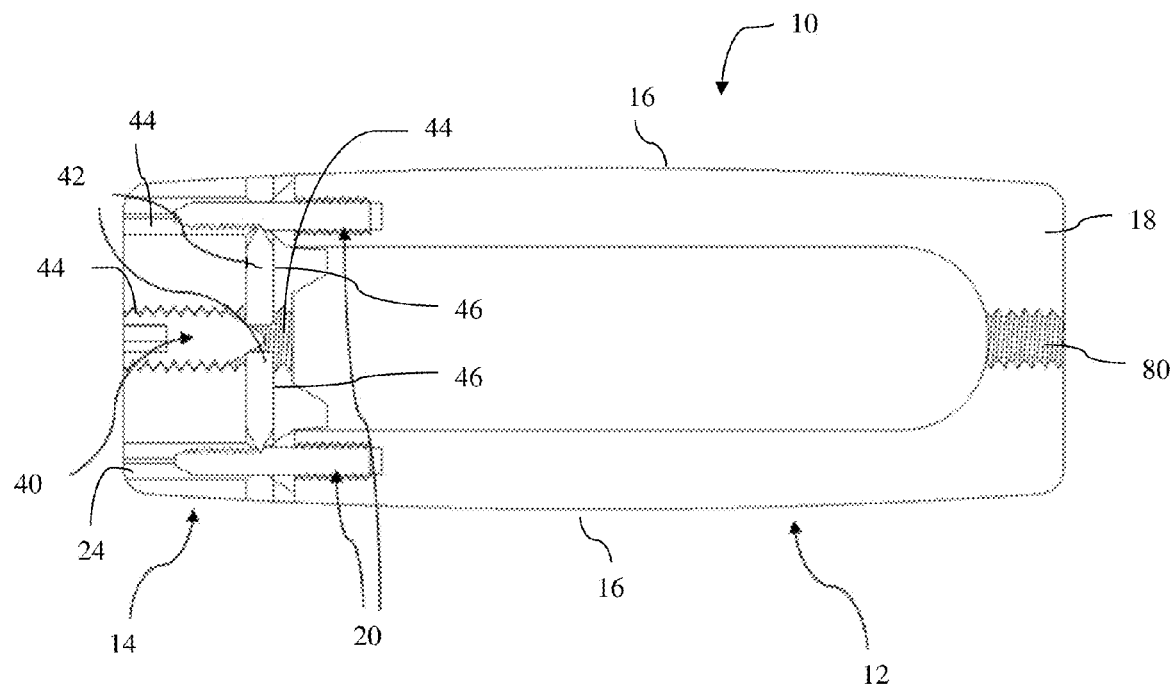
FIG. 6 is a top view, in partial cross section, of the interbody fusion implant of FIG. 1 illustrating the locking features between the base and closure members after engagement and locking according to an aspect of the present invention.

As best shown in FIGS. 5-6, a secondary locking mechanism may also be provided according to an aspect of the present invention, such as (by way of example only) equipping the closure member 14 with an actuating element 40 and a pair of transverse pins 42. The actuating element 40 is disposed within a longitudinal recess 44 extending (by way of example only) along the longitudinal axis of the implant 10. The transverse pins 42 are disposed within corresponding transverse apertures 46 extending (by way of example only) generally perpendicularly from the longitudinal recess 44. As best shown in FIG. 5, prior to actuation (i.e. axial translation towards the interior of the implant 10), a trailing end 48 of the actuation element 40 extends slightly past the longitudinal recess 44 and a beveled leading end 50 is barely (if at all) in contact with the medial ends 48 of the transverse pins 42.

As best shown in FIG. 6, upon actuation, the trailing end 48 is moved axially within the longitudinal recess 44 such that the beveled leading end 50 forces the transverse pins 42 into axial translation within the transverse apertures 46 and into physical engagement with the locking pins 20 of the base member 12 which are disposed within the recesses 24 of the closure member 14. This action serves to form a secondary lock between the closure member 14 and the base member 12. The actuation element 40 may be any number of different mechanisms for driving the transverse pins 42 into the locked position against the locking pins 20, including but not limited to a set screw type component as shown in FIGS. 5-6. The serrations 38 of the locking pins 20 advantageously aid in establishing purchase with the pointed end of the transverse pins 42 to thereby augment the locking ability between the closure member 14 and base member 12. The serrations 38 may also be angled as shown in FIG. 6 in order to make them easier to insert within the recesses 24 than to remove from the recesses 24. The transverse pins 42 may be of a metallic construction to simultaneously serve as radiopaque markers to aid in the visualization of the closure member 14 or the implant 10 during and/or after implantation, particularly when the base member 12 and closure member 14 are constructed of radiolucent material, such as poly-ether-ether-ketone (PEEK) and/or other suitable biocompatible and radiolucent materials.

The actuation element 40 as described above provides a number of benefits, including allowing a final inspection of the base member 12 and closure member 14 before the actuation element 40 is advanced to the locking position shown in FIG. 6. As such, if the sizing or the position of the implant 10 is determined to be less than optimal or for whatever reason undesirable by the surgeon, they have the option of simply removing the closure member 14 without first needing to back out the actuation element 40 and disengage the transverse pins 42 from the locking pins 20. Another benefit is that, by positioning the actuation element 40 within the longitudinal aperture 44 of the closure member 14 during the introduction of the closure member, it prevents any bodily tissues from building up or becoming lodged in the longitudinal aperture 44. A still further benefit is that, once the fully assembled implant 10 is packed with fusion promoting material 52 (as illustrated in FIG. 3), the fusion promoting material does not have an aperture to allow for an egress route through the closure member 14.

Figure 7:
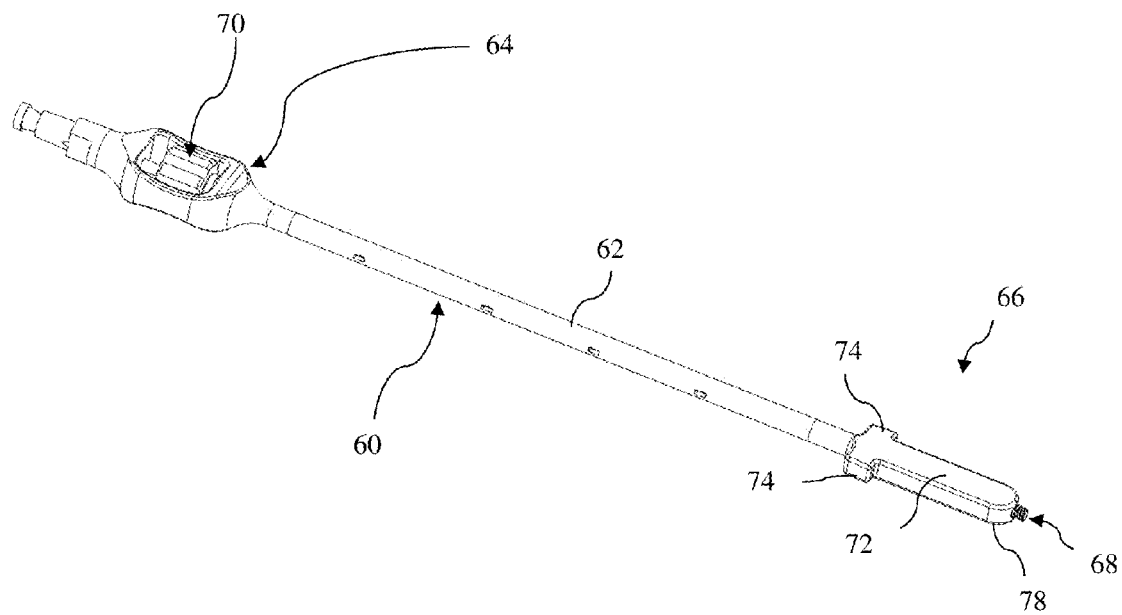
FIG. 7 is a perspective view of an inserter for use with the base member of the interbody fusion implant of FIG. 1 according to an aspect of the present invention.
Figure 8:
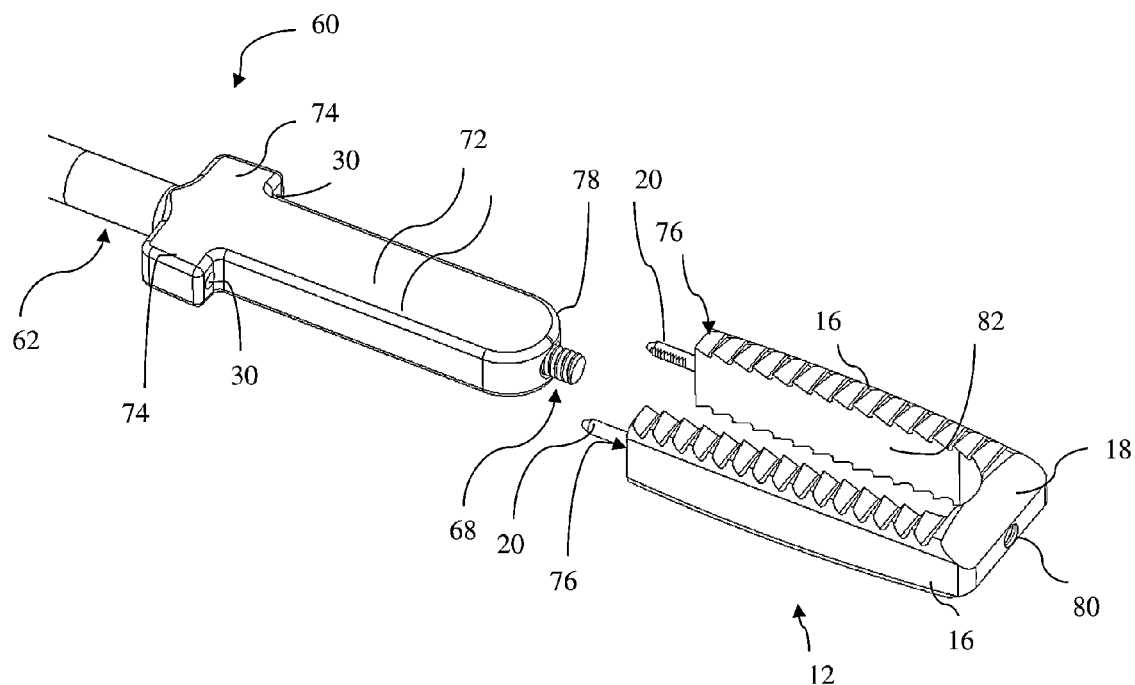
FIGS. 8 and 9 are perspective views of the inserter of FIG. 7 and the base member of FIG. 1 before and after, respectively, coupling together according to an aspect of the present invention.
Figure 9:
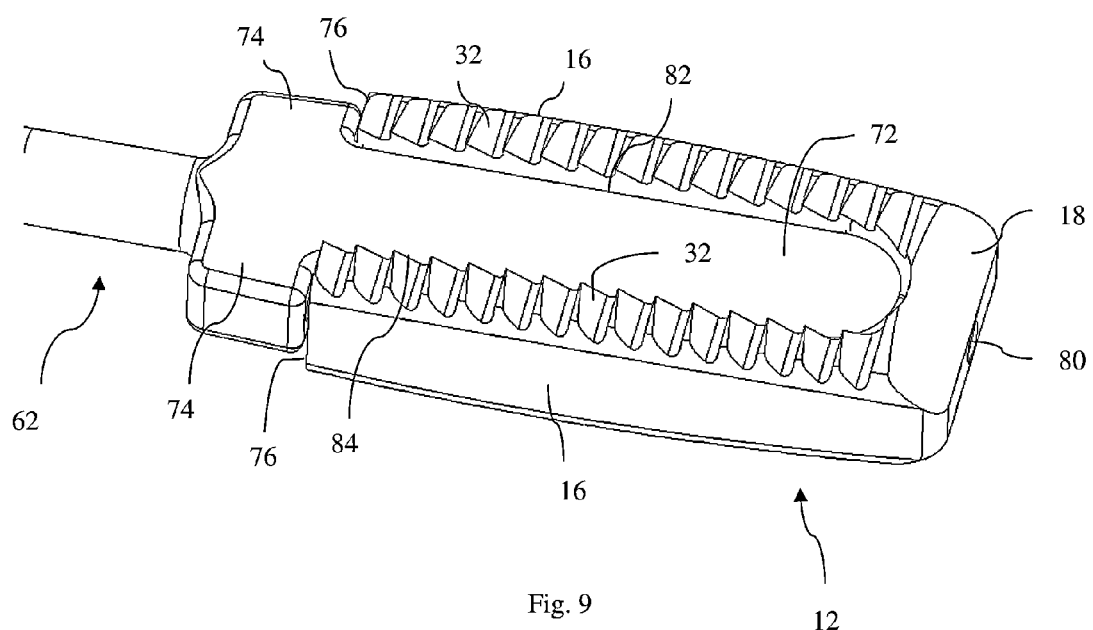

According to an aspect of the present invention, the base members 12 and closure members 14 shown herein may be introduced into an interbody space via any number of suitable insertion instruments. By way of example only, FIGS. 7-9 illustrate an inserter 60 for use in introducing the base member 12 of FIGS. 1-6 into an interbody space according to an aspect of the present invention. As best viewed in FIG. 7, the inserter 60 includes an elongated shaft 62 with a handle region 64 and an insertion region 66 disposed at either end. The elongated shaft 62 is hollow in construction and houses a coaxially aligned inner shaft having a threaded distal end 68 and a proximal end coupled to a thumb wheel 70 located in the handle region 64. The insertion region 66 includes a main body 72 and lateral members 74 extending generally laterally from the trailing end at the approximate junction with the elongated shaft 62. The main body 72 has a peripheral shape that is generally complimentary to the interior shape of the base member 12 as defined by the side walls 16 and end wall 18. The lateral members 74 are dimensioned to abut the trailing ends 76 of the side walls 16 when the main body 72 is positioned within the base member 12. The lateral members 74 have each have a recess 30 extending generally longitudinally within the lateral members 74 dimensioned to accommodate and receive the locking pins 20 of the base member 12 to facilitate engagement between the base member 12 and inserter 60. The threaded distal end 68 extends beyond the leading end 78 of the main body 72.

As best viewed in FIGS. 8-9, by rotating the thumb wheel 70, the threaded distal end 68 can be selectively engaged and disengaged with the corresponding threaded aperture 80 formed in the end wall 18 of the base member 12. More specifically, advancing the thread 68 into to base member 12 causes the base member 12 to be pulled towards the main body 72 of the inserter 60 until the inner surface 82 of the base member 12 is fully mated with the peripheral surface 84 of the inserter 60 as shown in FIG. 9. The advancement of the base member 12 toward the main body 72 of the inserter also results in the advancement of the locking pin 20 in the recesses 30 of the lateral member 74, thereby providing rotational stability during insertion into the patient. Once fully seated in this manner, the base member 12 is ready to be inserted into the interbody space according to an aspect of the present invention. After implantation, as will be described in greater detail below, the inserter 60 can be selectively disengaged from the base member 12 by reversing the direction the thumb wheel 70 and thus disengaging the threaded distal end 68 from the corresponding recess 80. This movement will also withdraw the locking pin 20 form the recesses 30 of the lateral members 74.

According to an aspect of the present invention, the complimentary shape of the insertion region 66 relative to the base member 12 bolsters the structural integrity of the base member 12 during the process of implantation. More specifically, the elongated and open nature of the generally U-shaped base member 12 causes it to be relatively weak in terms of resisting sheer forces that may otherwise occur if the base member 12 were introduced by applying forces to one or both of the trailing ends 76 of the side walls 16 or only the end wall 18. Instead, the insertion region 66 is dimensioned to maximize the surface area between the main body 72 and the interior of the base member 12.

Figure 10:
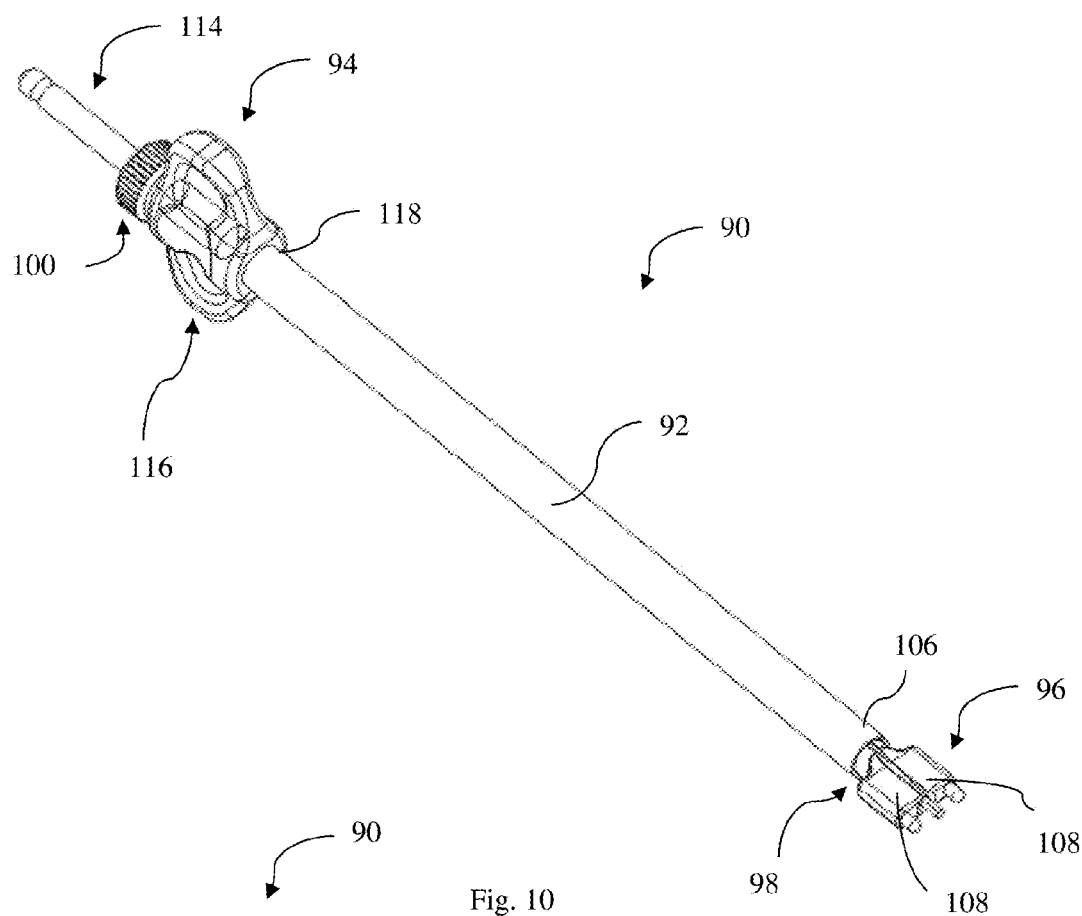
FIG. 10 is a perspective view of an inserter for use with the closure member of the interbody fusion implant of FIG. 1 according to an aspect of the present invention.
Figure 11:
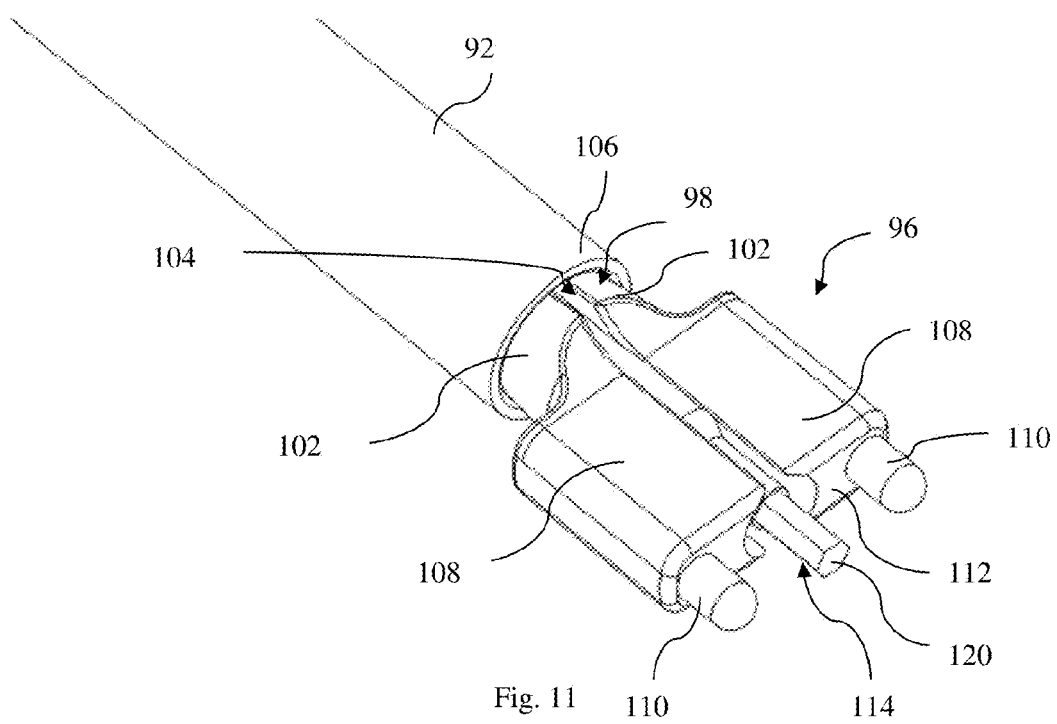
FIG. 11 is a perspective enlarged view of the distal end of the inserter of FIG. 10 according to an aspect of the present invention.

FIGS. 10-13 illustrate an inserter 90 for the closure member 14 of FIGS. 1-6 according to an aspect of the present invention. As shown in FIGS. 10-11, the inserter 90 includes an elongated shaft 92 with a handle region 94 and an insertion region 96 disposed at either end. The elongated shaft 92 is hollow in construction and houses a coaxially aligned inner shaft 98 having a proximal end coupled to a knurled member 100 of the handle region 94 and a pair of distal ends 102 separated by a gap 104 extending a predetermined distance within the distal end 106 of the hollow elongated shaft 92. The inner shaft 98 also includes a pair of arm members 108, with each arm member 108 having a prong member 110 extending longitudinally away from a distal surface 112. The inner shaft 98 is also generally hollow in construction and houses a driver member 114 (by way of example only, a hex driver) having a proximal end extending beyond the handle region 94 and a distal end extending beyond the arm members 108 of the inner shaft 98.

In addition to the knurled element 100, the handle region 94 also includes a counter-torque element 116 coupled to the proximal end 118 of the elongated shaft 92. The counter-torque element 116 allows the surgeon to hold the elongated shaft 92 relatively stationary as the knurled member 100 is rotated relative to the elongated shaft 92 or vice versa. Although not shown, the interior of the proximal end 118 of the elongated shaft 92 has a threaded configuration which cooperates with a threaded configuration located on the inner shaft 98 adjacent to the knurled member 100. By rotating the inner shaft 98 relative to the elongated outer shaft 92, the insertion region 96 will be translated axially towards the distal end of the elongated shaft 92. This, in turn, will cause the arm members 108 to be moved towards one another, thereby reducing the gap 104.

Figure 12:
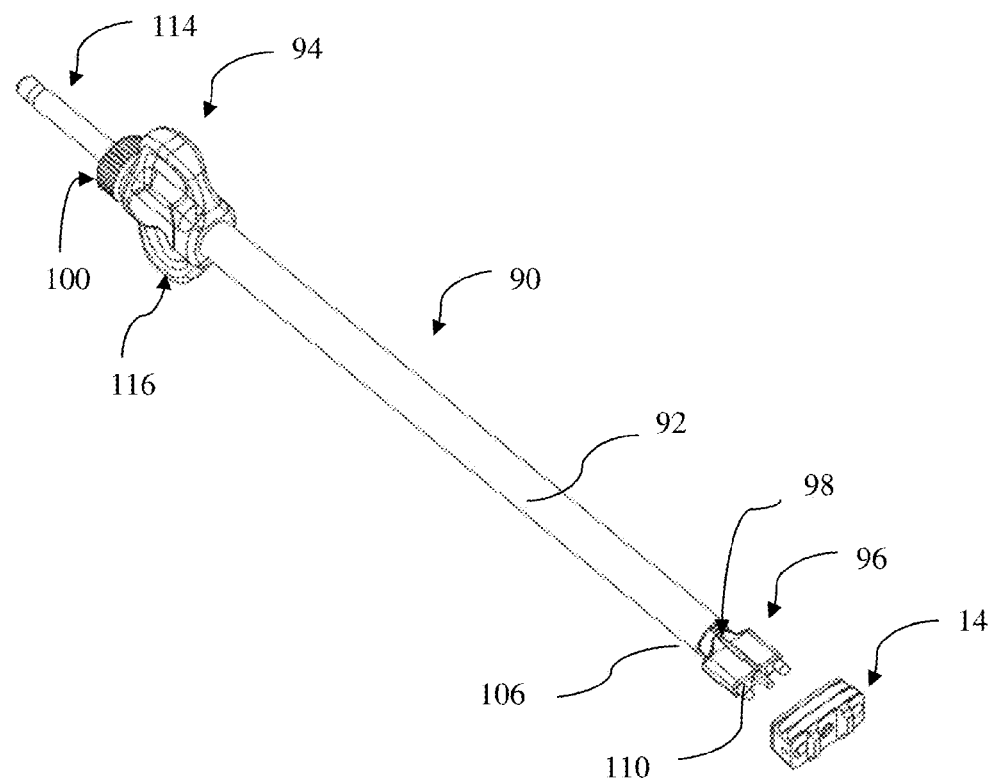
FIGS. 12 and 13 are perspective views of the inserter of FIG. 10 and the closure member of FIG. 1 before and after, respectively, coupling together according to an aspect of the present invention.
Figure 13:
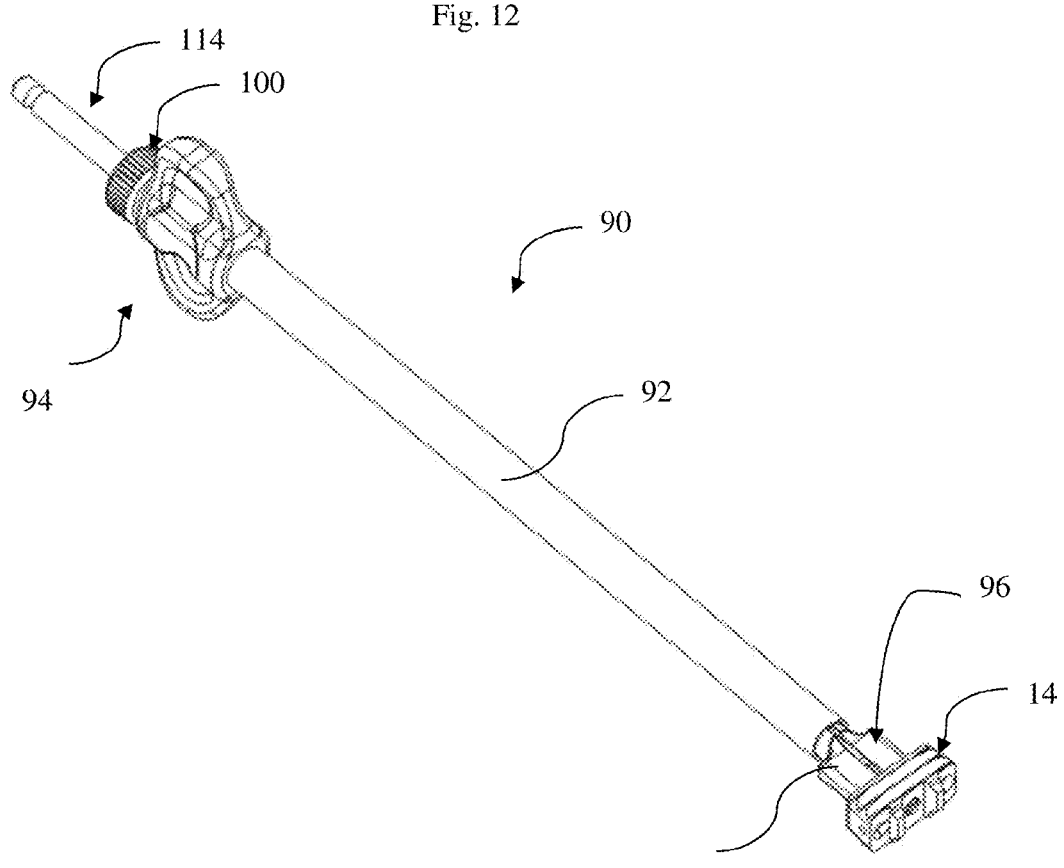
Figure 14:
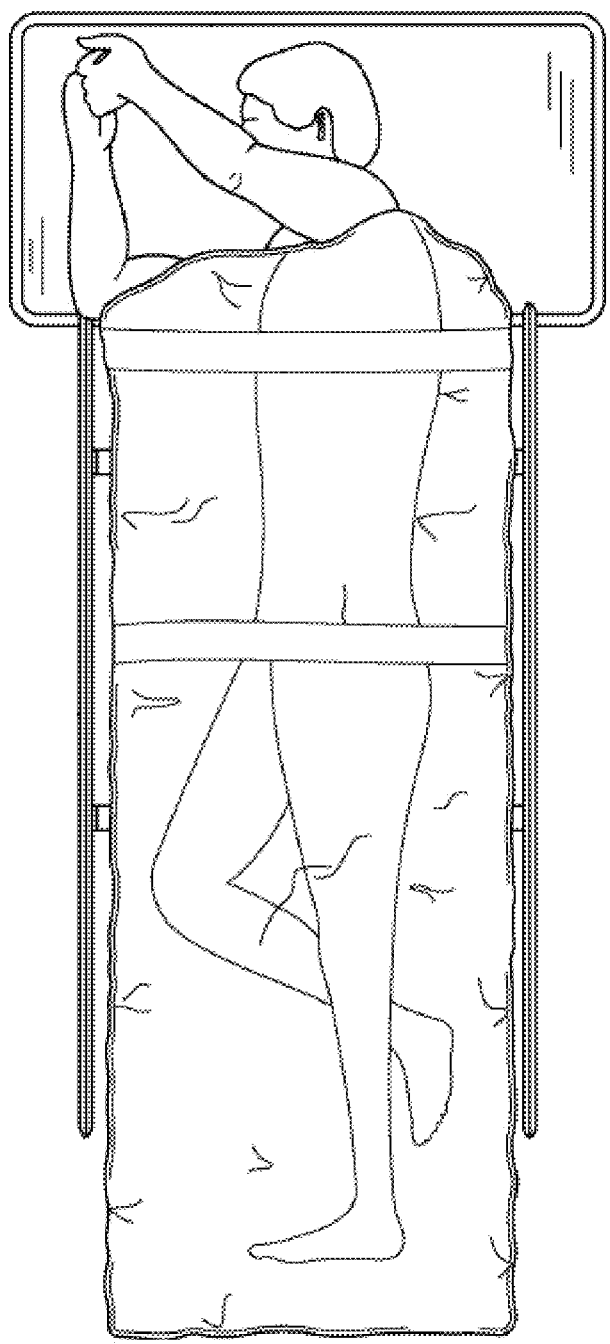
FIG. 14 is a top view of a patient in the lateral decubitus position in preparation for lateral access surgery.
Figure 15:
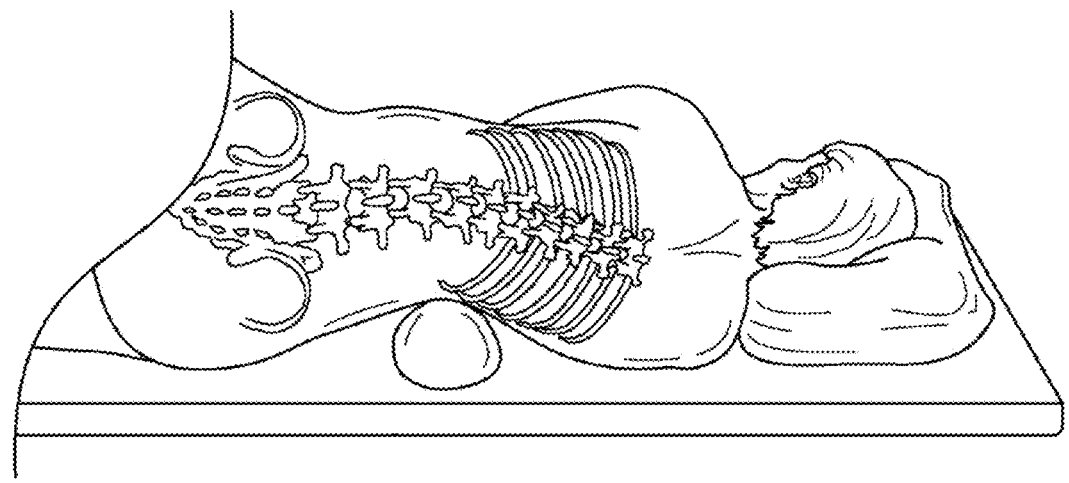
FIG. 15 is a posterior view of a patient in the lateral decubitus position in preparation for lateral access surgery illustrating aspects and general positioning of the lumbar and thoracic spine.
Figure 16:
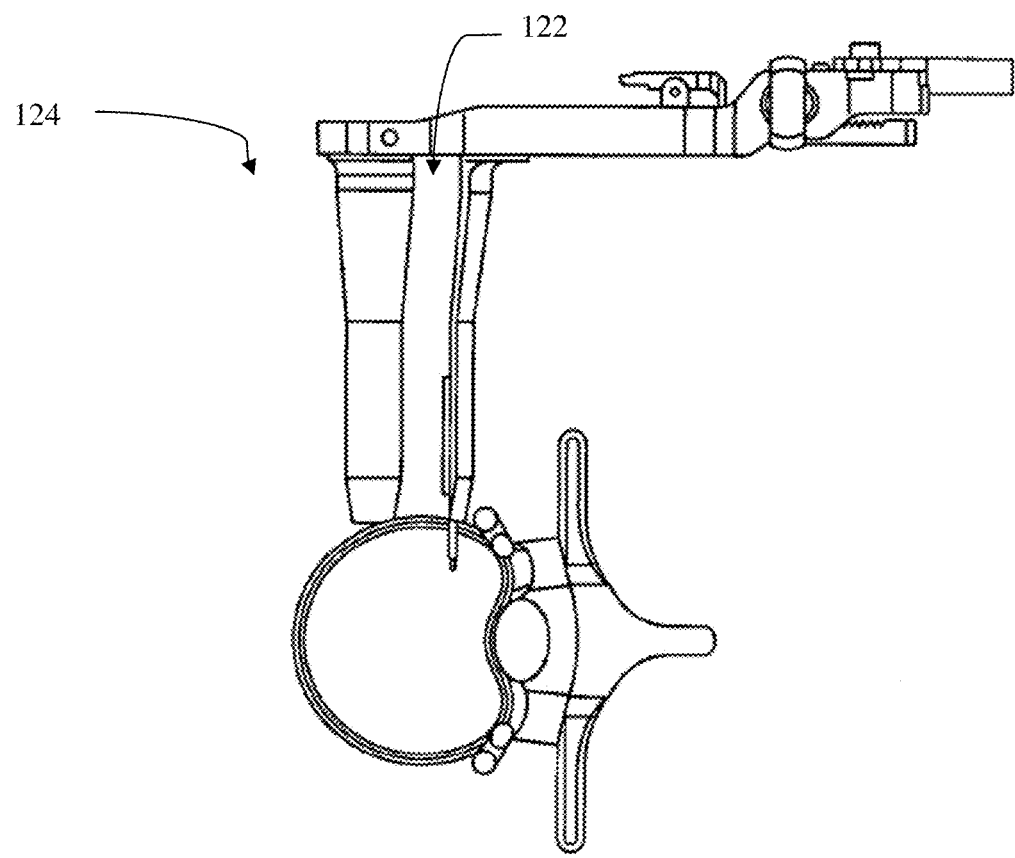
FIG. 16 is a side view of a prior art retractor system positioned laterally relative to the patient's lumbar spine in preparation for the implantation of the interbody fusion implant of FIG. 1 according to an aspect of the present invention.
Figure 17:
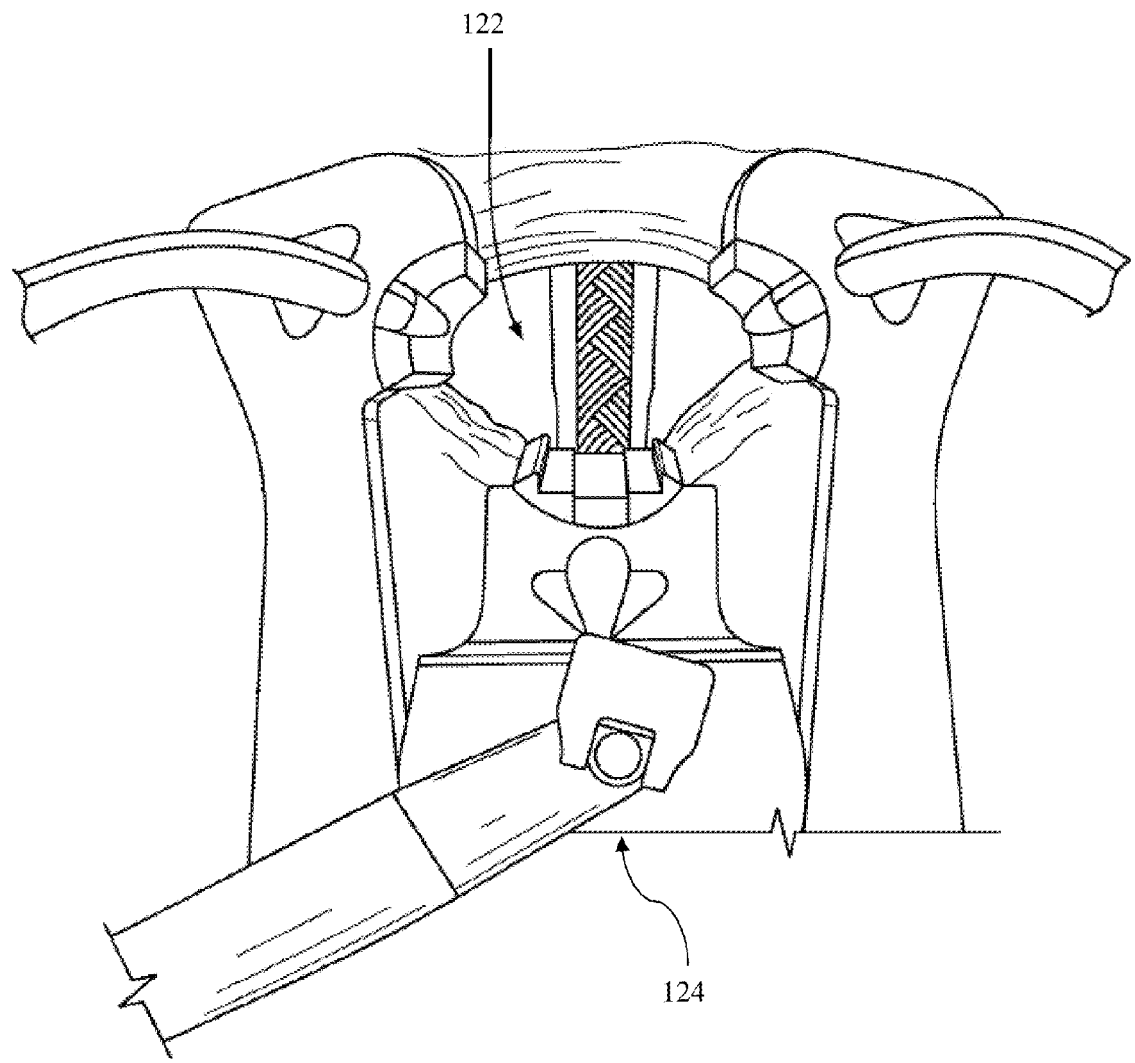
FIG. 17 is a lateral view down an operative corridor established by the prior art retractor system of FIG. 16 before an annulotomy and discectomy are performed in preparation for the implantation of the interbody fusion implant of FIG. 1 according to an aspect of the present invention.

As best viewed in FIGS. 12-13, to couple the inserter 90 to the closure member 14, the inserter 90 is advanced such that the prong members 110 on the arm members 108 extend into the recesses 24 for the locking pins 20 (see FIG. 5). At that point, with the closure member 14 in abutment with the distal surface 112 of the arm members 108, the knurled member 100 may be rotated relative to the counter-torque element 116 (or vice versa) such that the arm members 108 are forced towards one another and thereby exert a compression force between the prong members 110 which acts upon the closure member 14 via the recesses 24 to temporarily lock the closure member 14 to the inserter 90. Once fully seated in this manner, the closure member 14 is ready to be inserted into the interbody space according to an aspect of the present invention, namely, to engage and then lock with the base member 12. After implantation, as will be described in greater detail below, the inserter 90 can be selectively disengaged from the closure member 14 by reversing the direction the knurled member 100 relative to the anti-torque element 116 and thus disengaging the prongs 110 from the corresponding recesses 24. Before doing so, however, the driver member 114 may be optionally employed to drive the actuation element 40 of the closure member 14 as described above in order to selectively deploy the transverse pins 42 with the goal of providing a secondary locking between the closure member 14 and the base member 12. The driver 114 is shown, by way of example only, with a hexagonal shape rod 120 dimensioned to engage with the proximal end of the actuation element 40 to engage and/or disengage the locking mechanism.

The inserter 90 thus provides the dual advantages of providing both a mechanism to affix the inserter 90 to the closure member 14 as well as the ability to engage and operate the actuation element 40 to lock the closure member 14 to the base member 12. That said, it will be appreciated that the inserter 90 can be used for the purpose of inserting the closure member 14 into the disc space without having the ability to lock the closure member 14 to the base member 12, such as where the secondary locking features (e.g. transverse pins 42 and actuation element 40) are not required. Although shown and described in this specific manner, it will be appreciated that the closure member 14 may be coupled to the inserter 90 in any number of suitable manners, including but not limited to the same or similar mechanism as used in FIG. 9, namely, a threaded rod that threads into a corresponding threaded hole. It is also contemplated to construct the closure member 14 to include two different sized threaded holes, one for the actuation element 40 and one for an additional threaded rod 68 as described above.

Figure 18:
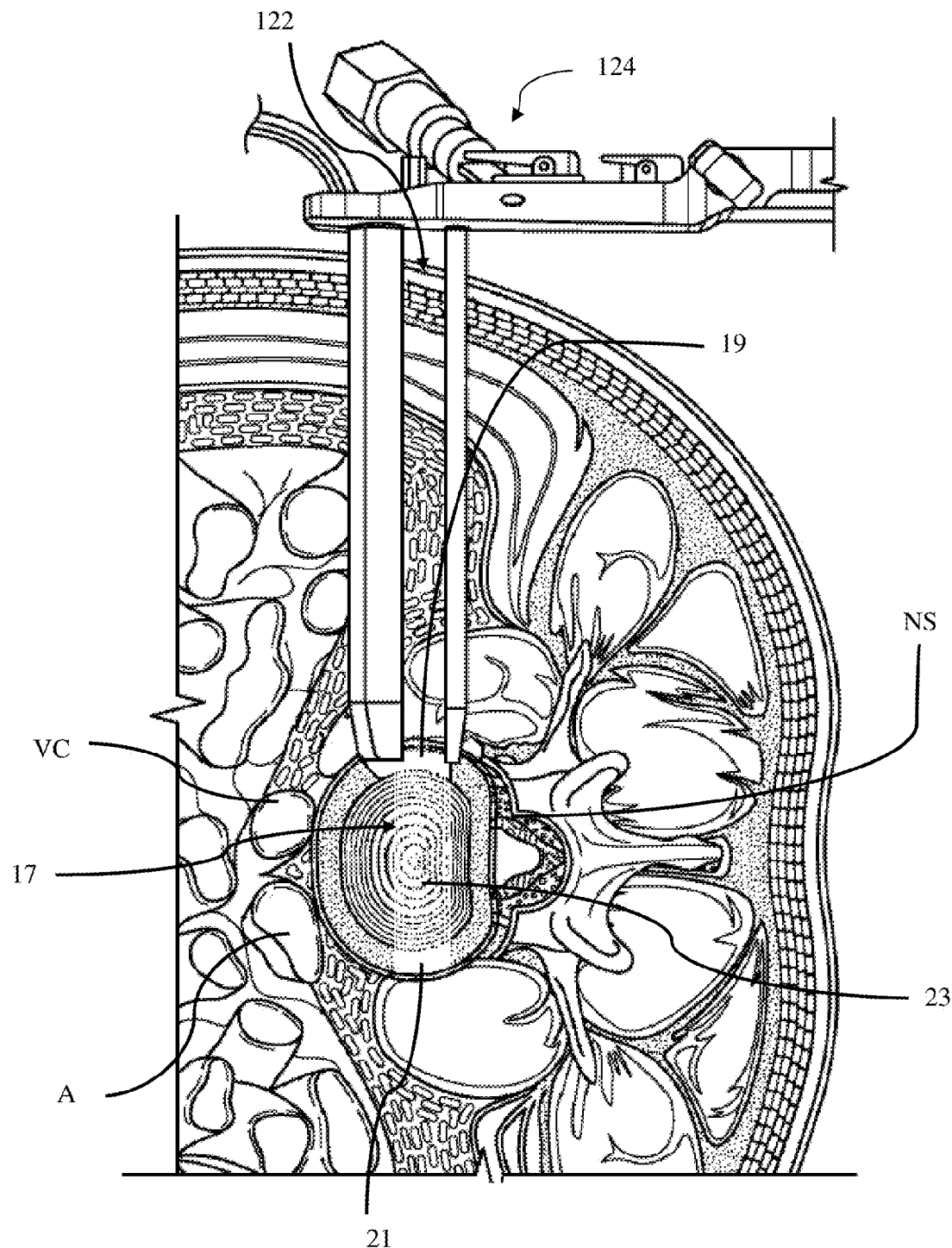
FIG. 18 is a cross sectional view of a patient during lateral access surgery after an annulotomy and preliminary discectomy have been performed in preparation for the implantation of the interbody fusion implant of FIG. 1 according to an aspect of the present invention.
Figure 19:
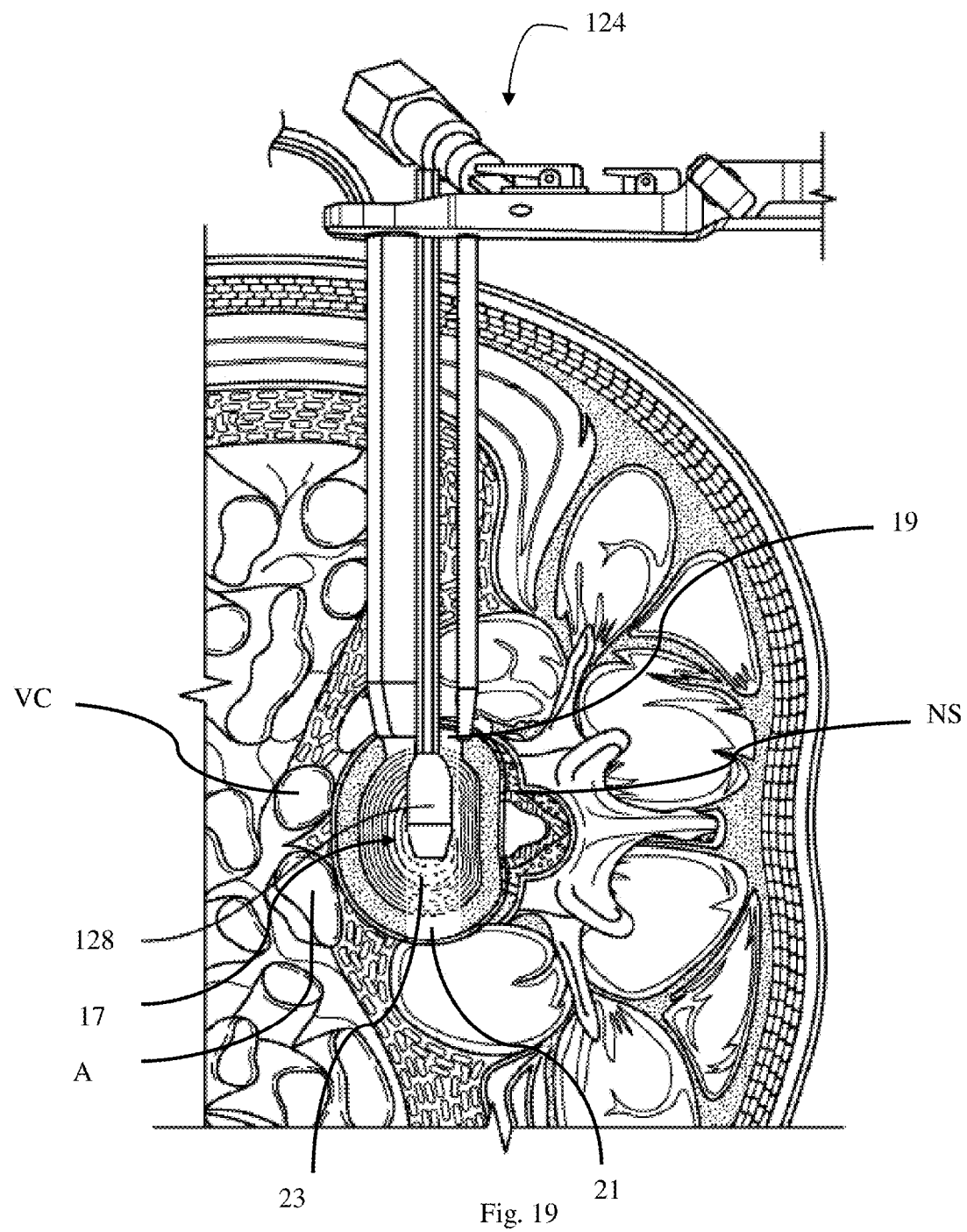
FIG. 19 is a cross sectional view of a patient during lateral access surgery illustrating the optional step of sizing/distracting the disc space before introducing the base member of FIG. 1 according to an aspect of the present invention.

The methodology associated with using the implant 10 during lateral access surgery according to an aspect of the present invention will now be described with reference to FIGS. 14-23, as well as the flow chart in FIG. 24. The first step involves gaining lateral access to the patient's lumbar or thoracic spine (step 130 in FIG. 24). This is performed by first (FIGS. 14-15) positioning the patient in the lateral decubitus position and then (FIGS. 16-17) establishing a lateral operative corridor 122 via the introduction of an access system such as the prior art retractor 124 shown by way of example only. With the operative corridor 122 established, an annulotomy and preliminary discectomy (steps 132, 134 in FIG. 24) must then be performed with the goal of creating an implant region 17 as shown in FIG. 18 capable of receiving a fully assembled implant 10 according to an aspect of the present invention. The implant region 17 preferably extends from the ipsilateral cortical bone region 19 to the contralateral cortical bone region 21 and the intervening cancellous bone region 23 of the underlying vertebral body. (Although shown fully removed on the contralateral bone region 21 in the interest of clarity, the annulus in that area may simply be "released" (cut but not fully removed) in order to accommodate at least a portion of the leading end of the base member 12.)

The next step (136 in FIG. 24) involves the process of sizing the base member 12 to ensure the desired restoration of disc height, sagittal and coronal balance, etc. . . . This can be facilitated by (FIG. 19) using a sizer/distractor instrument 128 for the purpose of identifying the proper amount of disc height restoration as well as loosening up the joint to facilitate the introduction of the base member 12. Depending upon the pathology and anatomy, the base member 12 may be selected having any of a variety of suitable heights, lengths, widths, lordotic tapers, coronal tapers, etc. . . . . Based on the ability to select an optimally sized closure member 14 after the fusion promoting material has been packed into the base member 12, it may be possible to have base members 12 of relatively standard or uniform length (albeit with varying height, width and curvature dimensions) in order to minimize the inventory required for surgery, as well as reduce the amount of time required for selecting a base member 12. The key is that the leading end of the base member 12 be positioned at least partially on the contralateral cortical region 21, as will be discussed in greater detail below.

Figure 20:
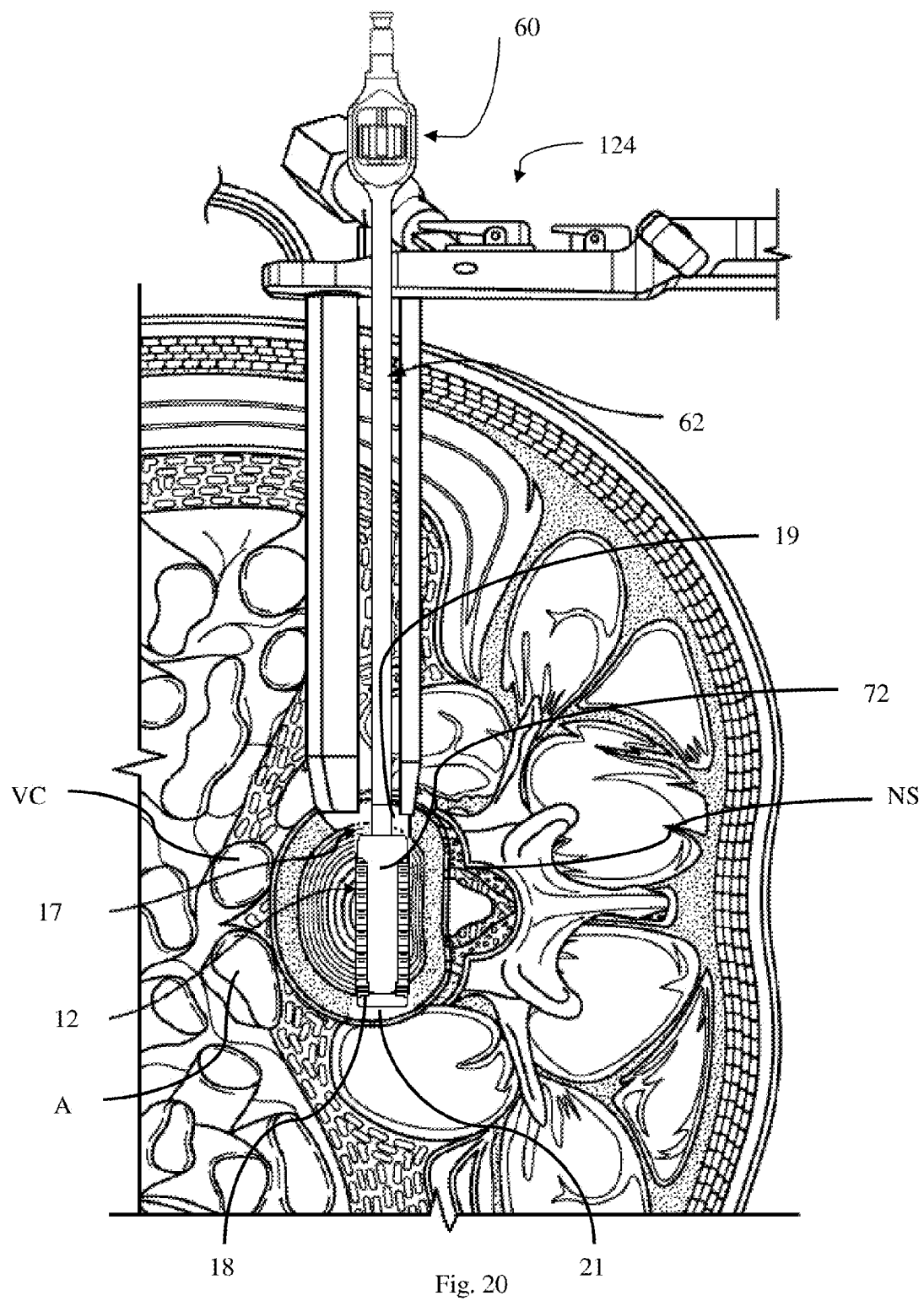
FIG. 20 is a cross sectional view of a patient during lateral access surgery illustrating the step of introducing the base member of FIG. 1 with the associated inserter of FIG. 7 according to an aspect of the present invention.
Figure 24:
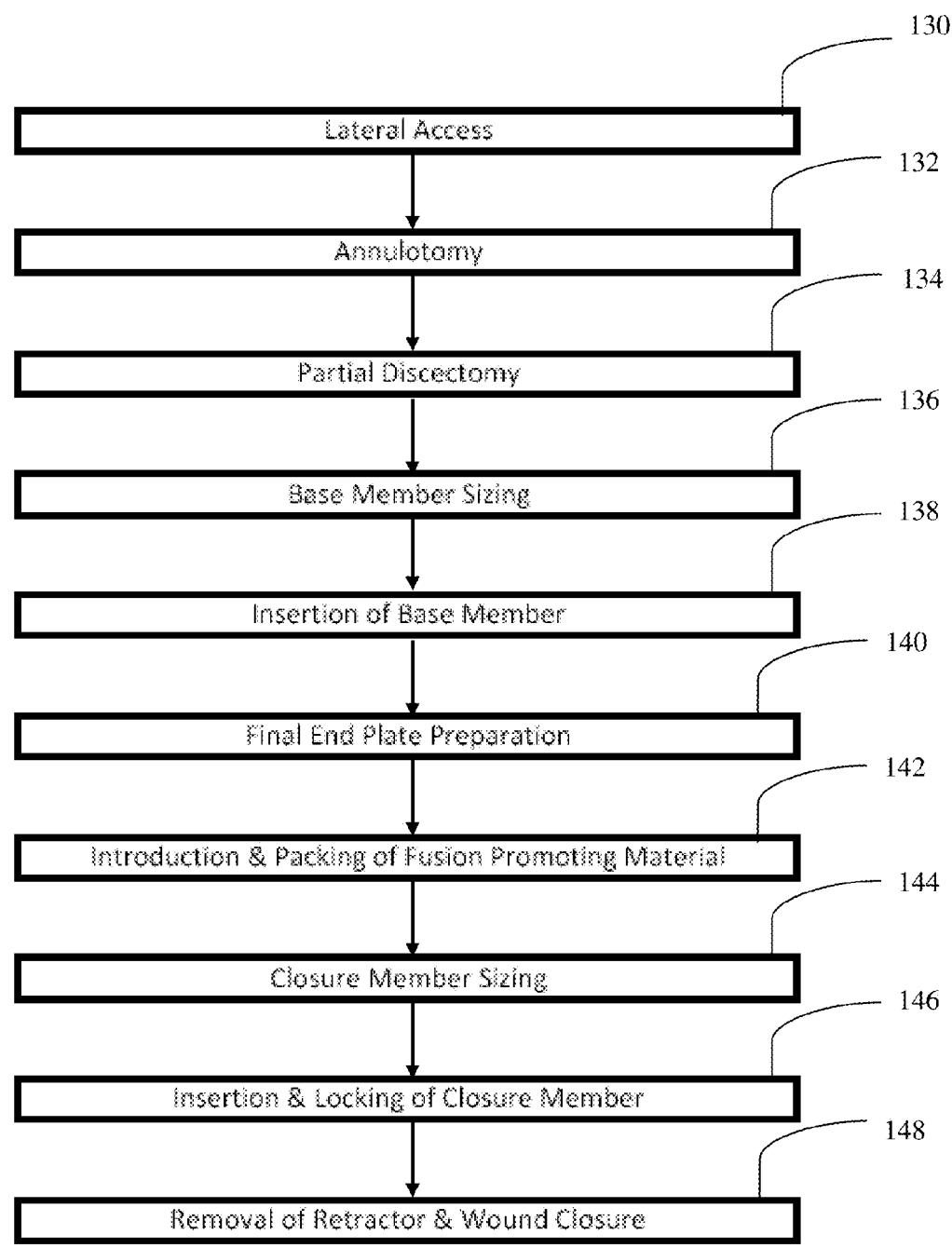
FIG. 24 is a flow chart describing the method steps involved in implanting an interbody fusion implant according to an aspect of the present invention.
Figure 25:
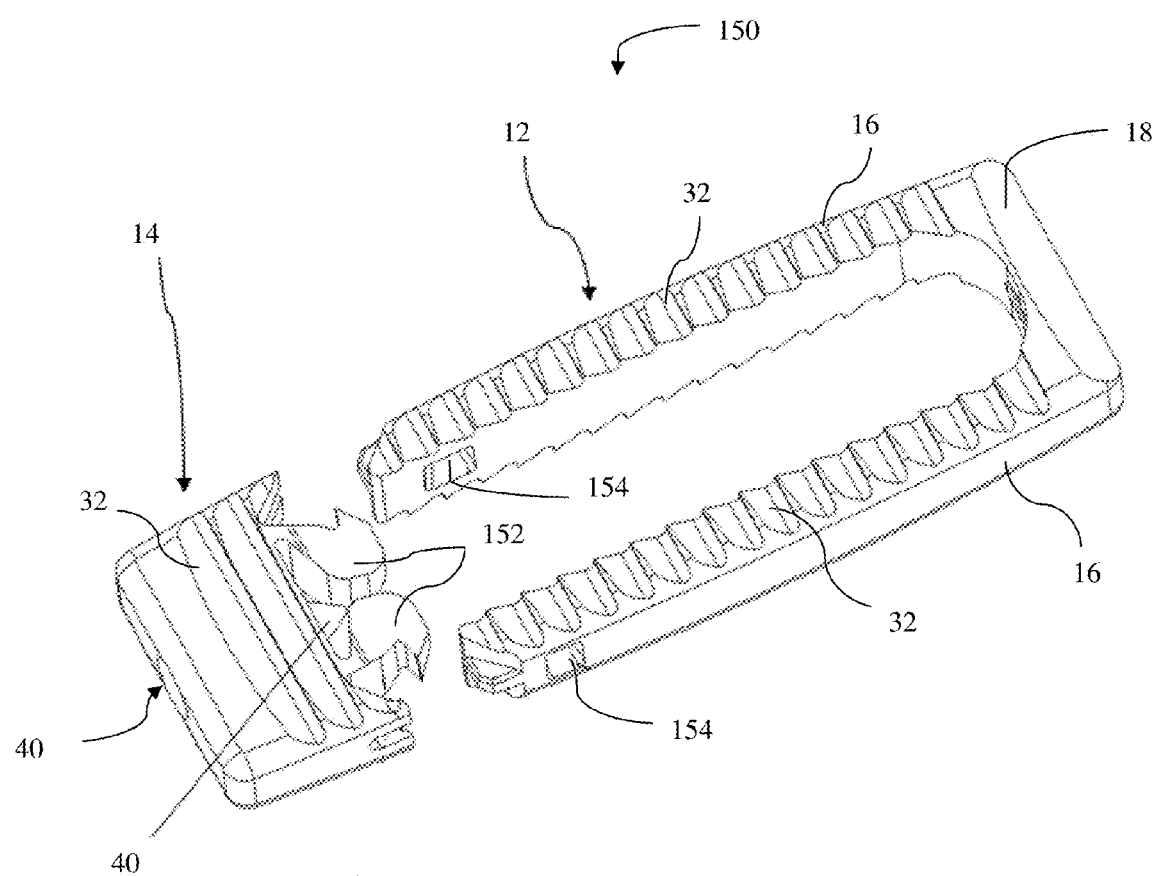
FIG. 25 is a perspective exploded view of an interbody fusion implant including a base member and closure member according to another aspect of the present invention.
Figure 26:
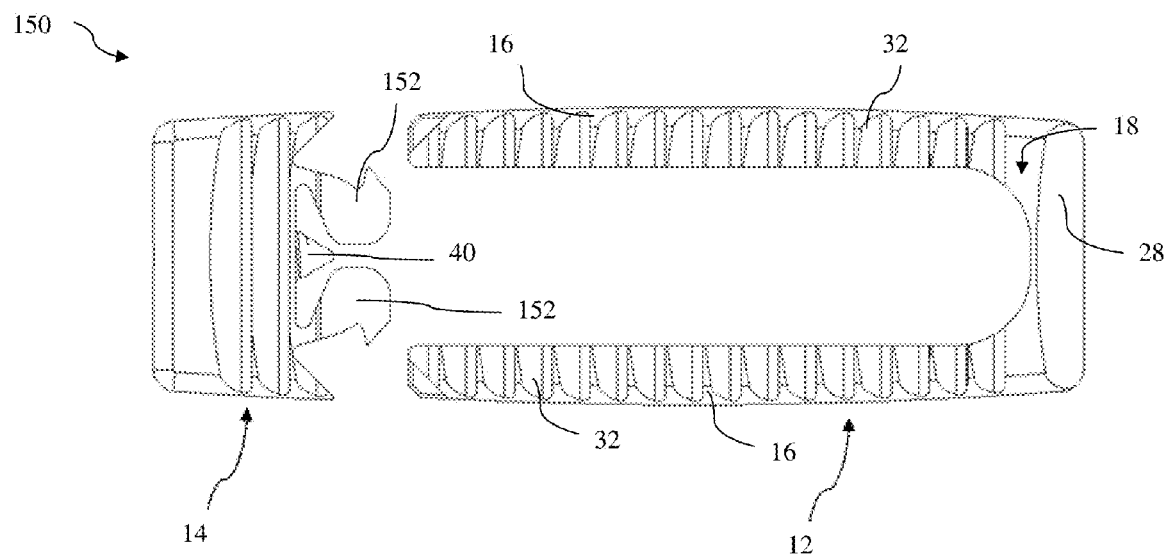
FIG. 26 is a top exploded view of the base member and closure member of FIG. 24 before engagement and locking together according to an aspect of the present invention.
Figure 27:
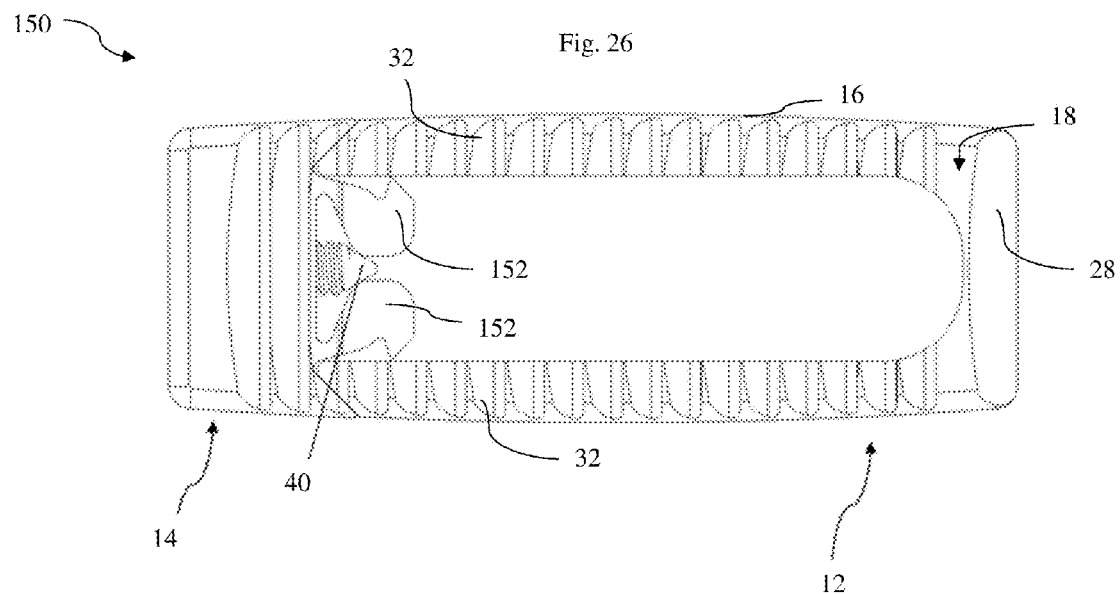
FIG. 27 is a top view of the base member and closure member of FIG. 24 after engagement and during the process of locking together according to an aspect of the present invention.
Figure 28:
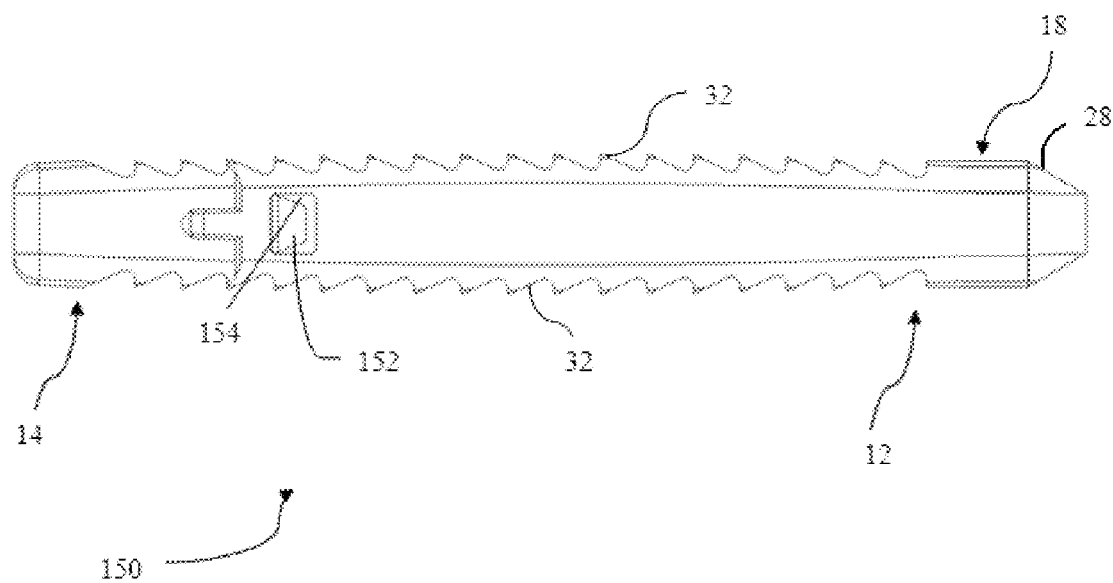
FIG. 28 is a side view of interbody fusion implant of FIG. 24 after locking the closure member to the base member according to an aspect of the present invention.
Figure 29:
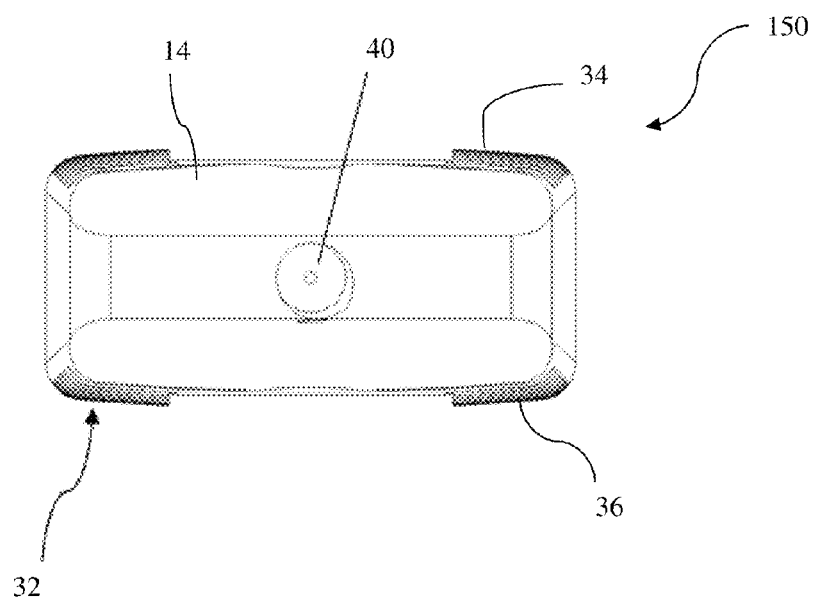
FIG. 29 is an end view of the closure member of FIG. 24 illustrating the engagement features for coupling the closure member to an inserter as well as the locking screw element for locking the closure member to the base member according to an aspect of the present invention.

Once the desired size of the base member 12 is determined (optimal or standard), the base member 12 may be inserted into the interbody space (step 138 in FIG. 24). This is accomplished by coupling the base member 12 to the inserter 60 and impacting it into the implant region 17 as shown in FIG. 20 via the use of any number of well known impaction tools (not shown). The base member 12 should be preferably located within the disc space (more specifically, within the implant region 17 shown in FIGS. 18-19) such that the leading end (end wall 18) is positioned at least partially on the contralateral cortical bone region 21 as shown in FIG. 20. With the base member 12 positioned in this manner, the inserter 60 may then be disconnected and the inserter 60 removed such that the base member 12 is the only element disposed in the disc space.

Figure 21A:
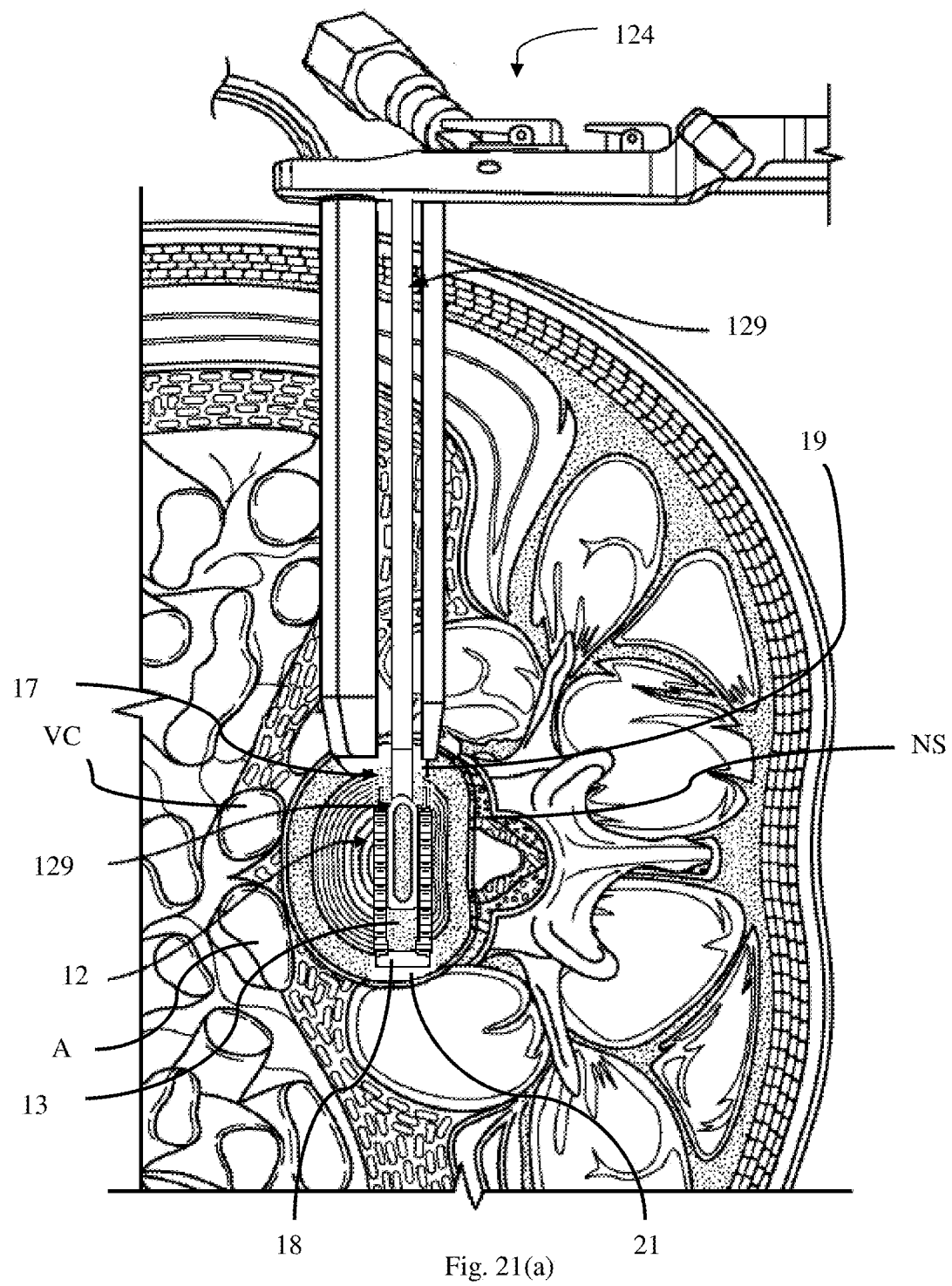
FIG. 21(a) is a cross sectional view of a patient during lateral access surgery illustrating the step of final end plate preparation after the introduction of the base member of FIG. 1, but before the introduction of the closure member of FIG. 1, according to an aspect of the present invention.
Figure 21B:
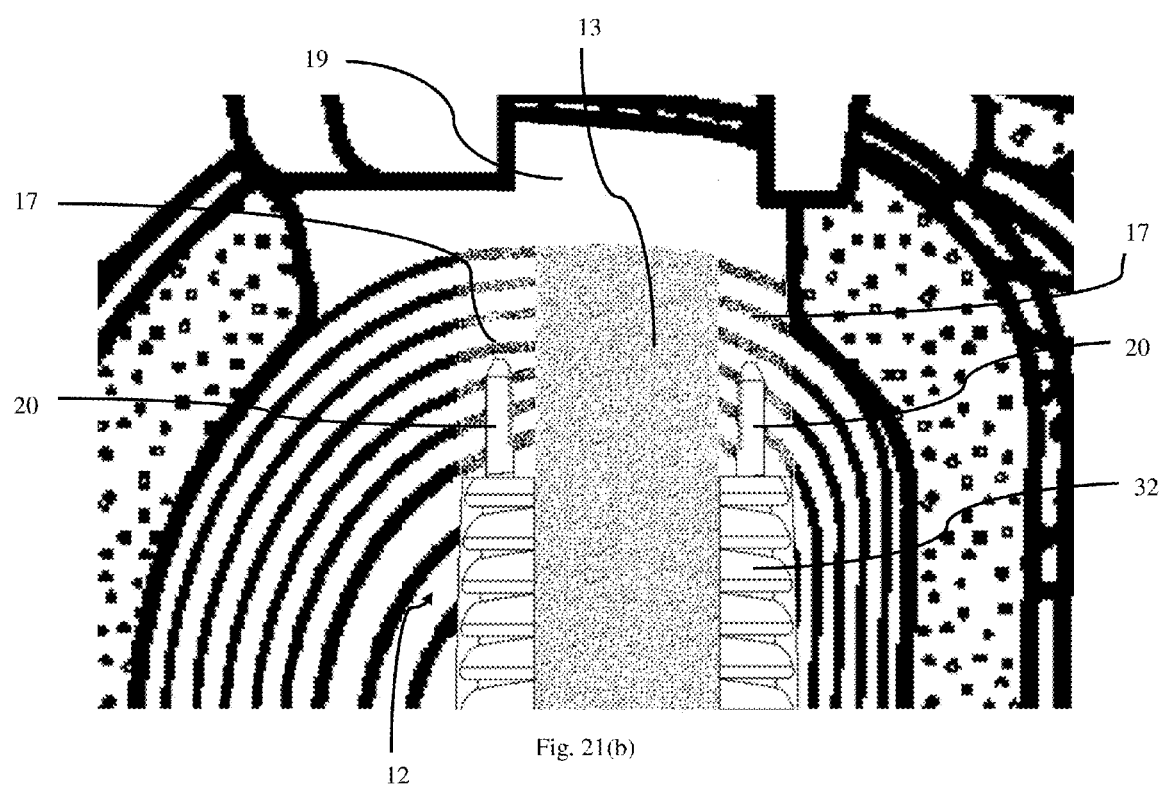
FIG. 21(b) is an enlarged view of the trailing end of the base member after final endplate preparation according to an aspect of the present invention.

FIGS. 21(*a*) illustrates the next step (140 in FIG. 24) of final endplate preparation, which may be accomplished via any number of well known endplate preparation tools, including but not limited to scraper 129 shown in FIG. 21(*a*), to create the fusion region 13 within the interior of the base member 12 and extending to the ipsilateral cortical bone region 19. In the interest of added clarity, FIG. 21(*b*) illustrates the trailing end of the base member 12 (and the surrounding area) after final endplate preparation to further detail the relation of the resulting fusion region 13 to the previously prepared implant region 17. According to an aspect of the present invention, the fusion area 13 is an exact, reproducible region separated from the neurovascular structures (aorta A, vena cava VC and posterior neural structures NS) by virtue of the side walls 16 and end wall 18 of the base member 12, thereby providing an added level of safety against the inadvertent positioning of the endplate preparation instruments past or outside the disc space during endplate preparation. Due to the protective feature of the base member 12, as well as the fact the upper and lower surfaces of the base member 12 rest upon the cartilaginous endplate exposed after the preliminary discectomy, the surgeon may be more aggressive in removing the cartilaginous endplates, intentionally scraping into the underlying cancellous bone to ensure sufficient bleeding for the fusion process to occur in a robust and timely manner.

Figure 22:
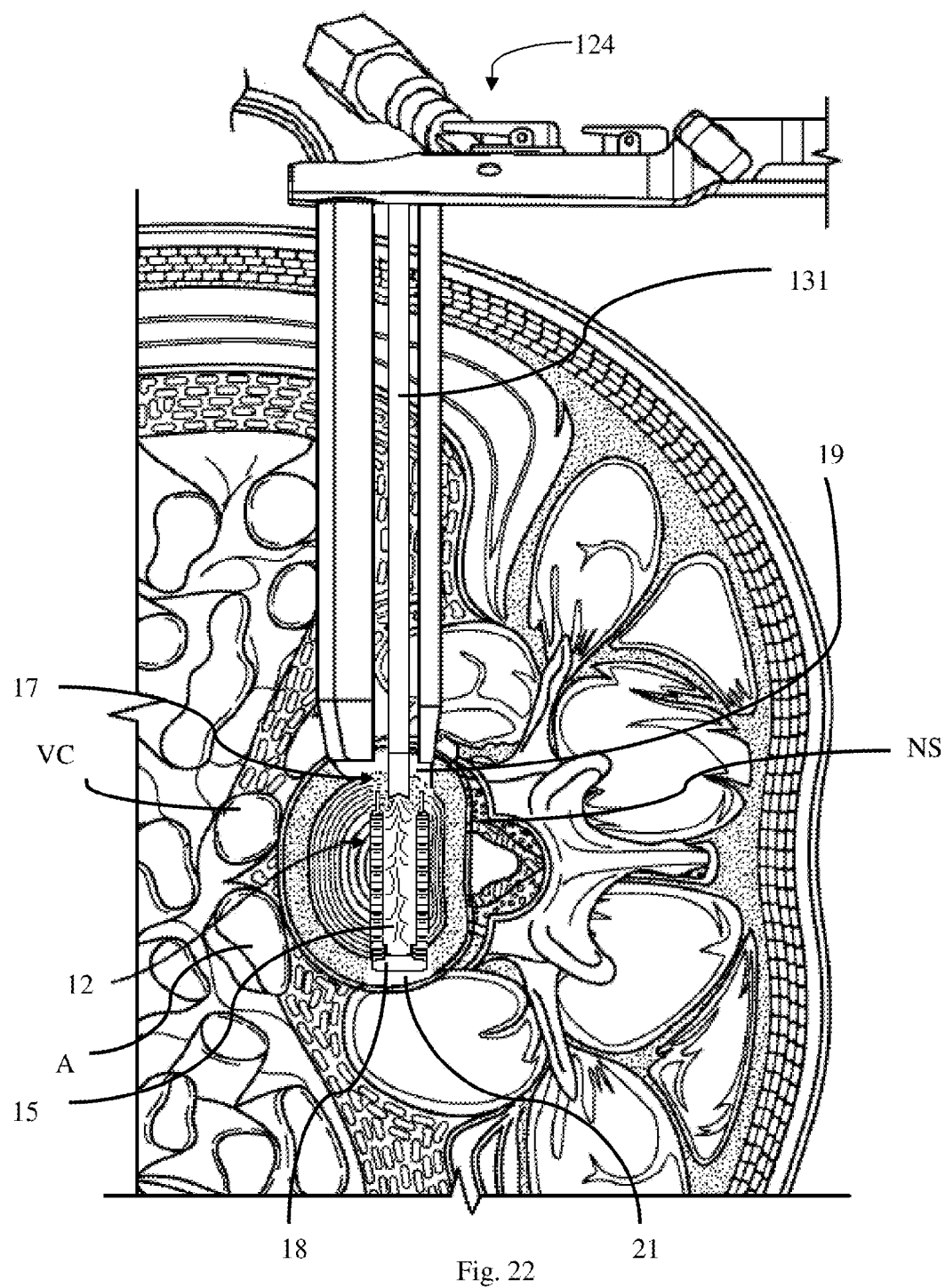
FIG. 22 is a cross sectional view of a patient during lateral access surgery illustrating the step of introducing fusion promoting material into the finally prepared disc space within the base member of FIG. 1 according to an aspect of the present invention.
Figure 23:
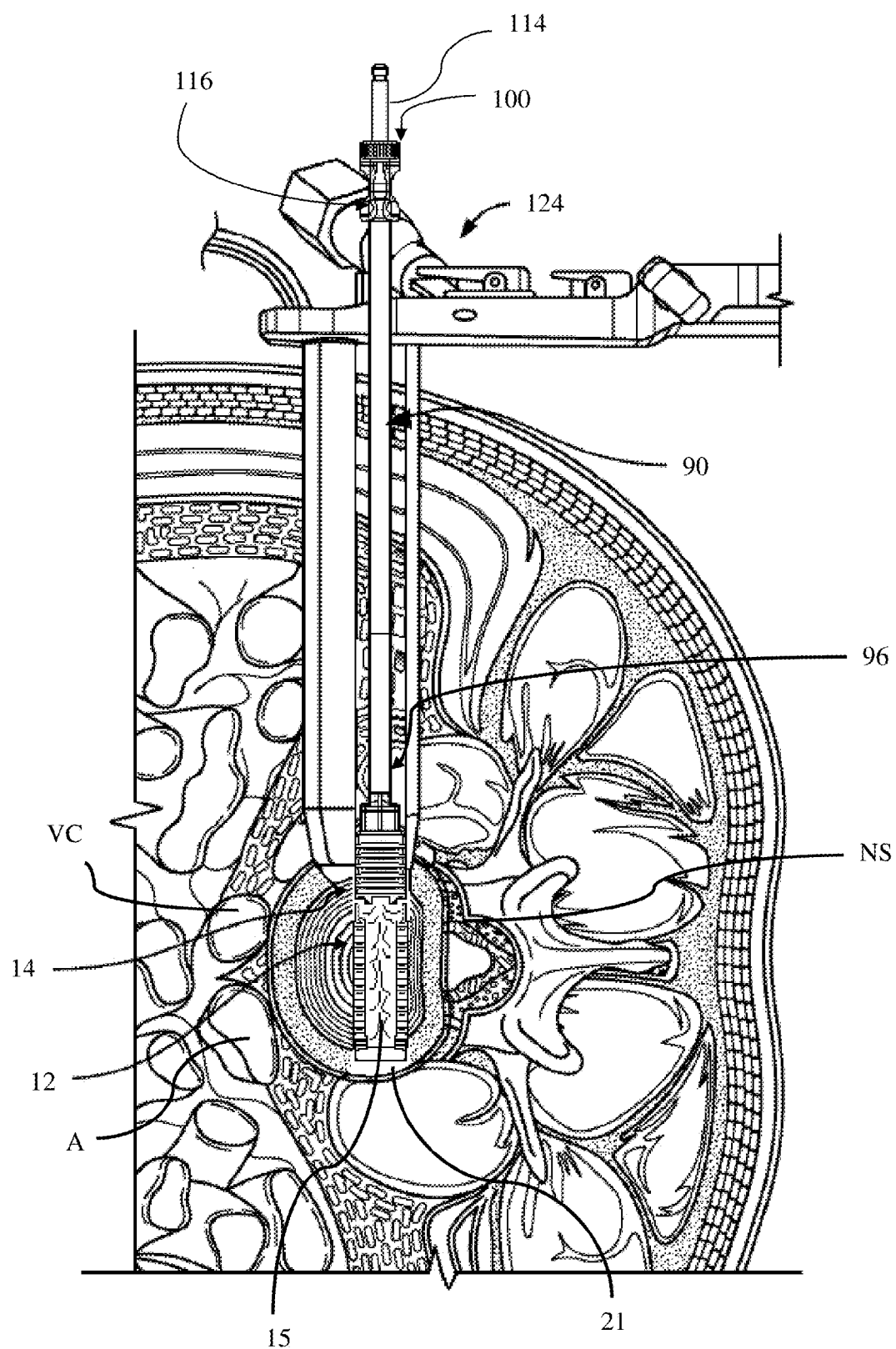
FIG. 23 is a cross sectional view of a patient during lateral access surgery illustrating the step of introducing the closure member of FIG. 1 for the engagement with the base member of FIG. 1 according to an aspect of the present invention.

With the base member 12 in position and the endplates fully prepared for fusion, the surgeon may (step 142 in FIG. 24) introduce and optionally pack any of a variety of fusion promoting materials within the base member 12 via (by way of example only) a packing funnel 131 such as shown generally in FIG. 22. Fusion promoting materials may include, but are not necessarily limited to, cancellous autograft bone, allograft bone, demineralized bone matrix (DBM), porous synthetic bone graft substitute, bone morphogenic protein (BMP), mesenchymal stem cells and/or combinations thereof and/or functional equivalents. Introducing this material after the base member 12 has been implanted is advantageous in that it increases the likelihood that the density of the fusion promoting material will be greater than if loaded and packed before introduction into the interbody space. This is because, with traditional implants which are packed prior to implantation, the impaction process tends to dislodge or loosen the fusion promoting substance. By packing the base member 12 after implantation, the surgeon can pack this material as densely as they can/wish before enclosing the cavity with the closure member 14 during lateral access surgery according to an aspect of the present invention.

Before enclosing the base member 12, the closure member 14 should preferably be sized (step 144 in FIG. 24) to ensure the optimal length, height, taper, etc. . . . for the desired amount of disc height restoration as well as (optionally) the preferred degree of sagittal and/or coronal re-alignment of the adjacent vertebral bodies. This can be facilitated by any number of suitable sizing tools (not shown), as well as via radiographic methods (e.g. MRI, X-ray, fluoroscope, etc. . . . ) and even any of a variety of depth gauges (not shown). The end goal is determine the optimal size to ensure that the resulting implant 10, after being formed in situ in the disc space, is positioned such that at least a portion of the leading end (end wall 18 of base member 12) and at least a portion of the trailing end (body 22 of the closure member 14) are positioned on the contralateral cortical bone region 21 and ipsilateral cortical bone region 19, respectively, as shown in FIG. 3 and partially in FIG. 23. This minimizes the risk of subsidence into the softer cancellous region. In this regard, both the base member 12 and the closure member 14 are in direct contact with upper and lower vertebral end plates, thereby bearing weight and sharing the loads from the end plates. Depending upon the pathology and anatomy, the closure member 14 may be selected having any of a variety of suitable heights, lengths, widths, lordotic tapers, coronal tapers, etc. . . . including those different from the base member 12 in order to (by way of example only) tailor the degree of lordosis (in the lumbar spine), kyphosis (in the thoracic spine) and/or coronal realignment (in the lumbar or thoracic spine) after the base member 12 has been implanted.

Once the optimal size of the closure member 14 has been determined, the closure member 14 may be inserted into the interbody space (step 146 in FIG. 24). This is accomplished by coupling the closure member 14 to the inserter 90 as shown and described above with reference to FIGS. 12-13 and then impacting it into the interbody space 126 and locking it to the base member 12 as shown and described with reference to FIGS. 5-6. FIG. 3 illustrates the end result, with the implant 10 formed in situ with the interbody space extending laterally with at least a portion of the leading end (end wall 18 of base member 12) resting on the contralateral cortical bone region 21 and at least a portion of the trailing end (body 22 of the closure member 14) resting on the ipsilateral cortical bone region 19. With the implant 10 filled with fusion promoting material 15 and enclosed via the combination of the closure member 14 and the base member 12, the retractor 124 may be removed and the wound closed (step 148 in FIG. 24) as is well known in the art.

Having described in detail the specifics of one type of implant 10 according to an aspect of the present invention, as well as the associated insertion instruments 60, 90 and methodology in lateral access surgery, a variety of additional implants forming aspects of the present invention will now be described. Based on many of the common features and/or functionality with the implant 10 described above, the following description and the associated drawings will not include specific references to associated inserters or much (if any) added detail regarding the associated methodology, as such is deemed duplicative and unnecessary.

FIGS. 25-29 illustrate an interbody fusion implant 150 including a base member 12 and closure member 14 according to another aspect of the present invention. The implant 150 is virtually identical to the implant 10 of FIGS. 1-23 except that the closure member 14 and base member 12 have a different locking mechanism. In particular, the closure member 14 includes a pair of bendable hook elements 152 extending towards the base member 12, and the side walls 16 of the base member 12 each include a recess 154 to receive the hook elements 152 after they have been forced into lateral movement by the axial advancement of the actuator element 40 of the closure member 14. The trailing end of the closure member 14 may be configured with any suitable engagement features for coupling to a suitable inserter, such as the slotted arrangement shown in FIG. 29 with the actuation element 40 disposed in the approximate midline. All other features in common with the implant 10 of FIGS. 1-23 are denoted with the same reference numbers and an explanation of then functionality may be ascertained with reference to the discussion of those similar features with reference to FIGS. 1-23.

Figure 30:
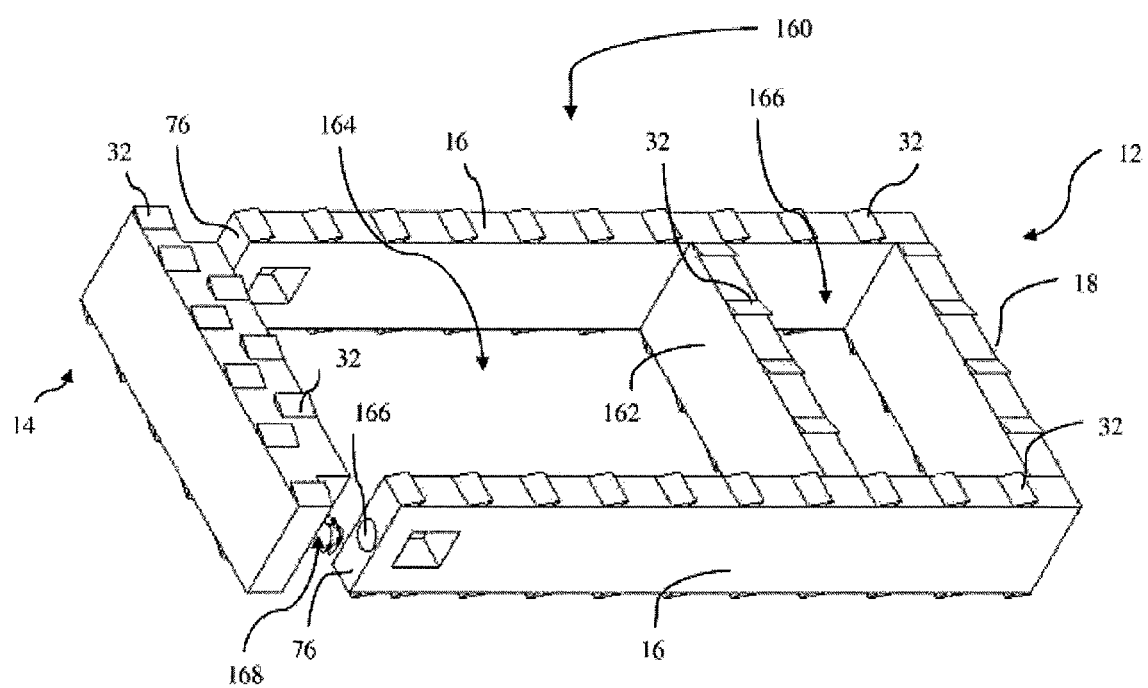
FIG. 30 is a perspective exploded view of an interbody fusion implant including a base member and a closure member according to yet another aspect of the present invention.
Figure 33:
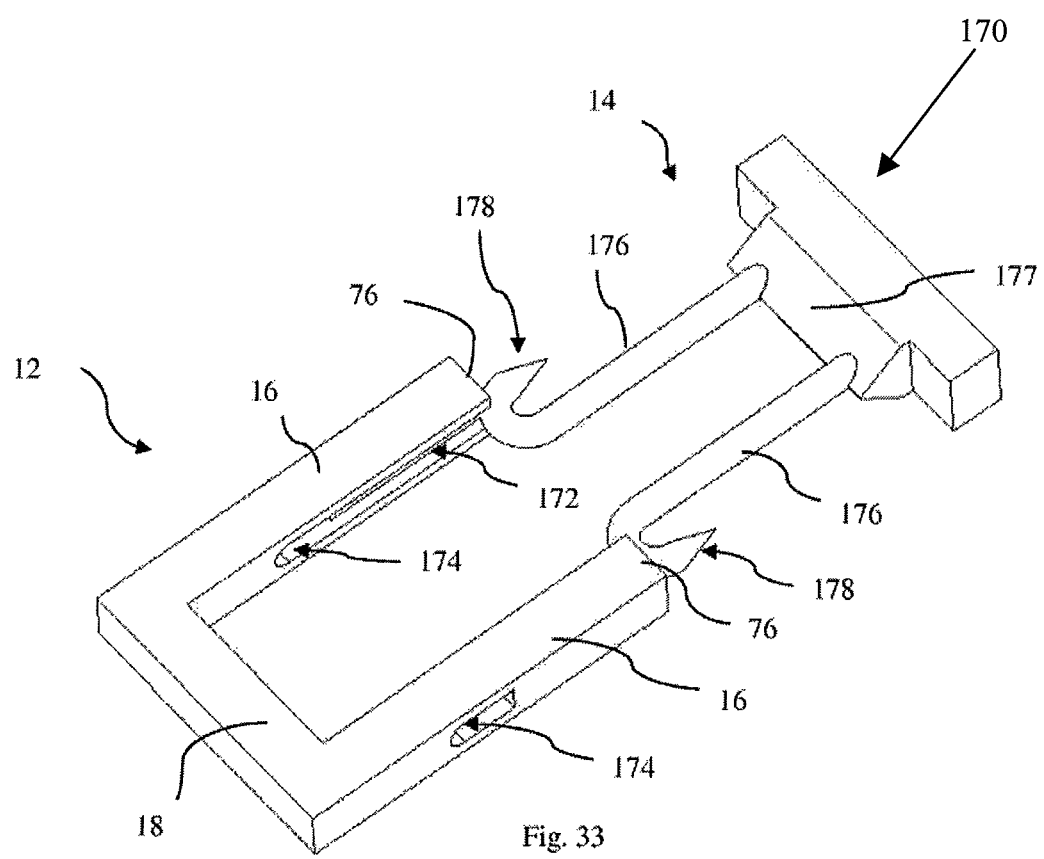
FIG. 33 is a perspective exploded view of an interbody fusion implant including a base member and a closure member according to a still further aspect of the present invention.
Figure 34:
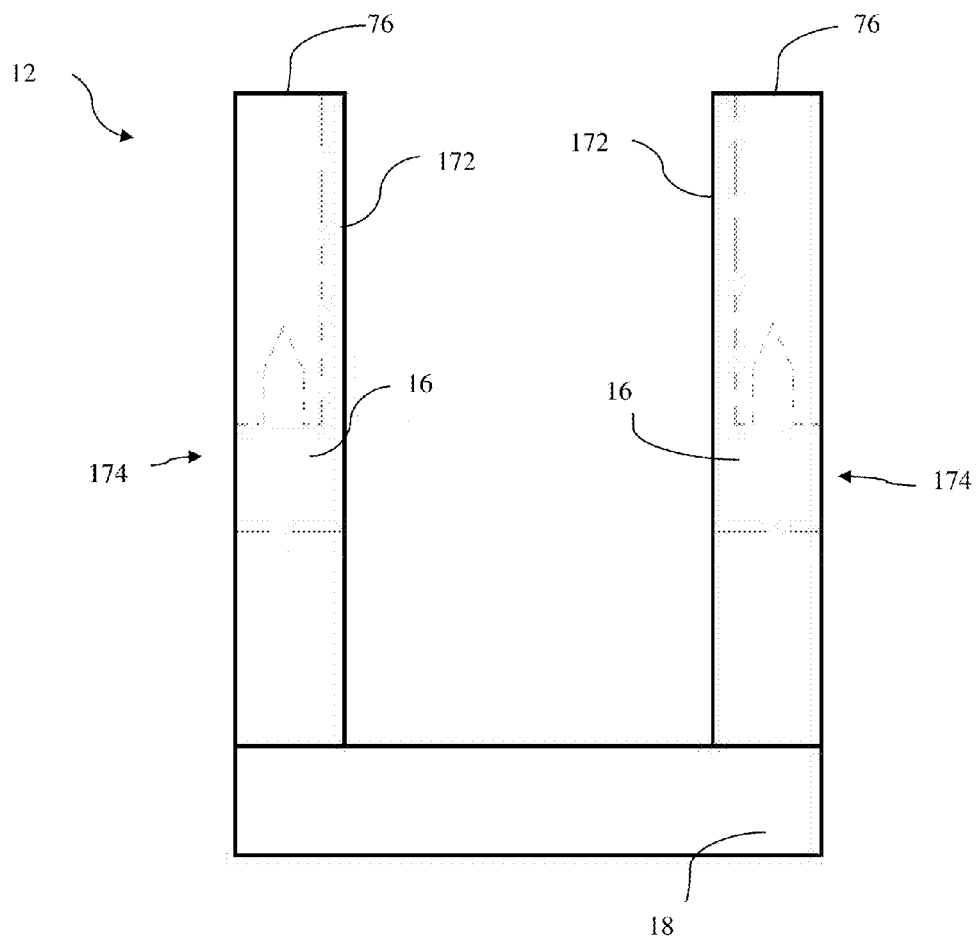
FIGS. 34 and 35 are top and end views, respectively, of the base member of FIG. 33 illustrating slot features for coupling the closure member to the base member according to an aspect of the present invention.
Figure 35:
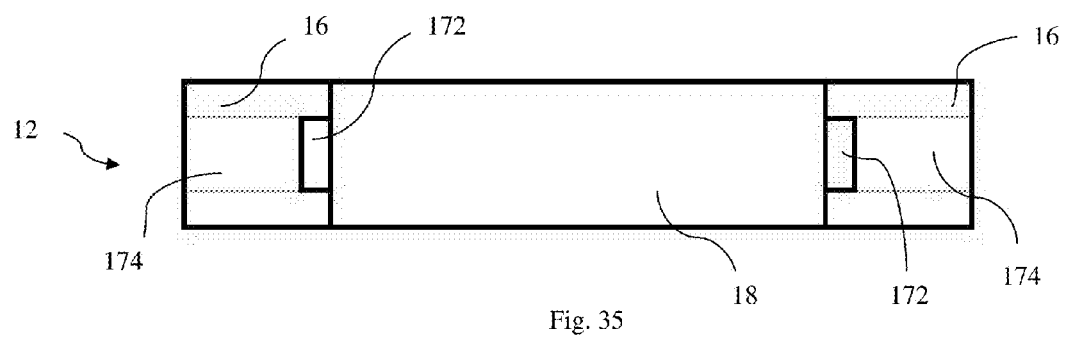
Figure 36:
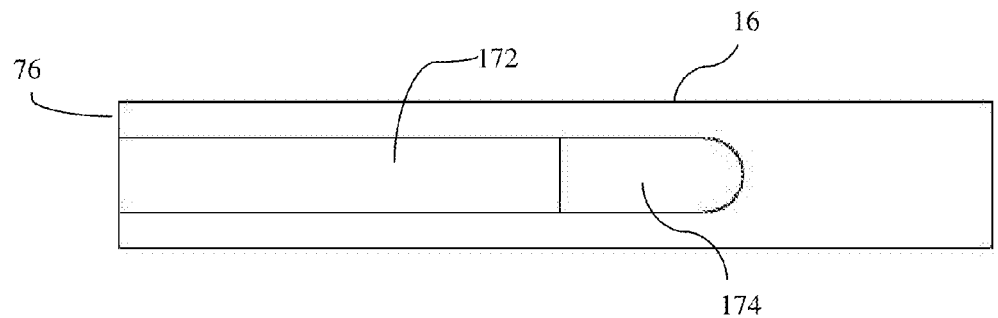
FIG. 36 is a side view of one arm of the base member of FIG. 33 further illustrating the slot features for engaging the closure member to the base member, as well as a recess for receiving locking prongs of the closure member of FIG. 33 according to an aspect of the present invention.
Figure 37:
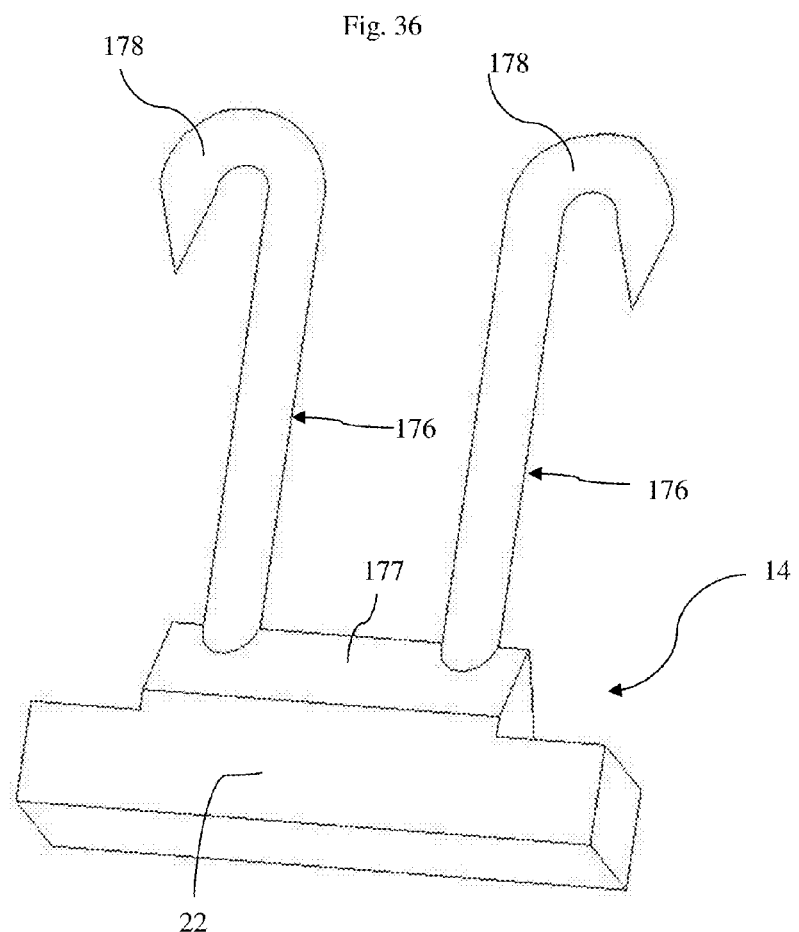
FIG. 37 is a perspective view of the closure member of FIG. 33 according to an aspect of the present invention.
Figure 38:
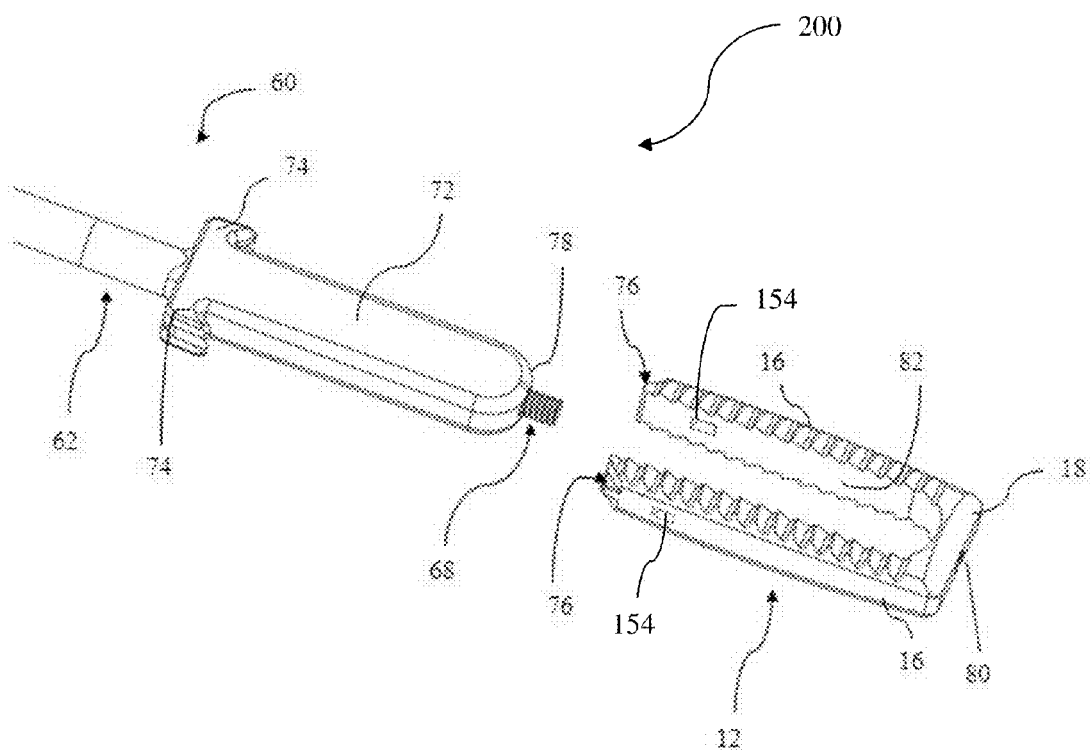
FIGS. 38 and 39 are perspective views of an inserter for use with the base member of FIGS. 25-29 before and after, respectively, coupling together according to an aspect of the present invention.
Figure 39:
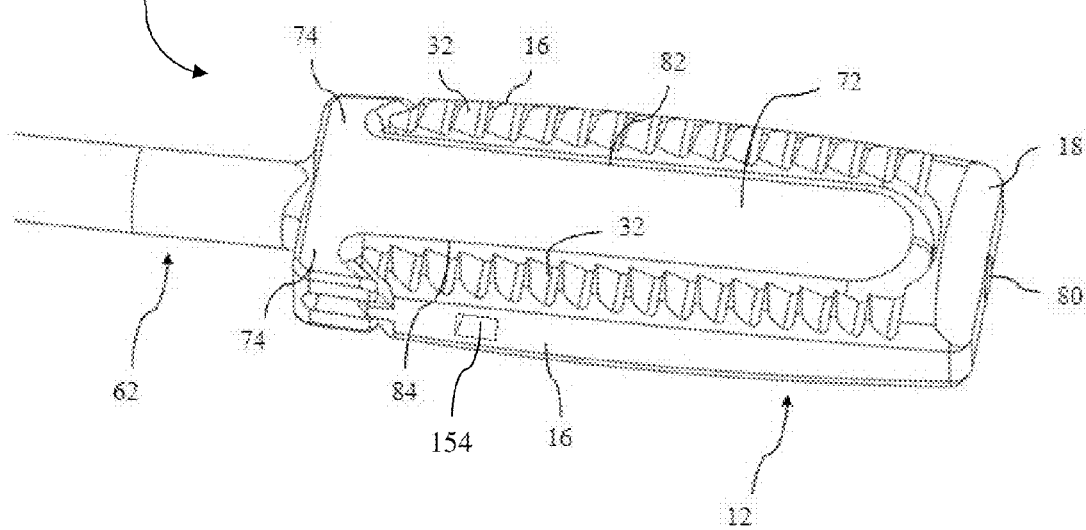

FIGS. 30-32 illustrate an interbody fusion implant 160 including a base member 12 and a closure member 14 according to yet another aspect of the present invention. The base member 12 has a rigid, elongated structure rectangular in nature. The base member 12 includes a supplemental wall 162 near the end wall 18 that defines a proximal opening 164 and a distal opening 166. The distal opening 166 may receive fusion promoting materials before the introduction of the base member 12, while the proximal opening 164 is dimensioned to receive fusion promoting materials after implantation of the base member 12 but before enclosure by the closure member 14. The closure member 14 includes two locking pins 168 extending longitudinally towards the base member 12, and the base member 12 includes two corresponding recesses 169 to receive the locking pins 168 for purposes of locking the closure member 14 to the base member 12. As best viewed in FIG. 32, the locking pins 168 have a generally "mushroom" shape with angled elements 167 that bend in order to permit the locking pin 168 to easily pass through the recesses 169 and then rebound and flare out to prevent the disengagement of the closure member 14 from the base member 12.

FIGS. 33-37 illustrate an interbody fusion implant 170 including a base member 12 and a closure member 14 according to a still further aspect of the present invention. The base member 12 has a generally U-shape with elongated slots 172 extending along the interior of the side walls 16 from the proximal end 76 to a point a predetermined distance towards the end wall 18. The side walls 16 also each include a recess 174 extending through the side wall 16 to intersect with the elongated slots 172. The closure member 14 includes a pair of elongated hooks 176 extending towards the base member 12. The elongated hooks 176 are generally compliant and bendable such that they will engage within the elongated slots 172 and deform slightly towards one another upon the application of axial force against the closure member 14 towards the base member 12. The distal region 178 of the hooks will pass along the slots 172 until they reach the recesses 174, at which point they will automatically rebound and move away from one another to force the distal regions 178 into the recesses 174 to lock the closure member 14 to the base member 12.

The closure member 14 also includes a wedge element 177 extending towards the base member 177 according to an aspect of the present invention. The wedge shape 177 allows for ease of insertion of the closure member 14 into the interbody space once the base member 12 has already been installed. The wedge shape 177 is an additional shape to the closure member 14, and once installed together with the base member 12, both the top and bottom surfaces 34, 36 are to be in direct contact with the end plates. The contacting surfaces 34, 36 allow the implant, both the closure member 14 and the base member 12, to the support weight and to share the loads from the endplates.

According to an aspect of the present invention, the implants described herein can be adapted for different applications and patient pathologies by selectively varying the heights, widths, lengths, lordotic taper and coronal taper in any suitable increment (e.g. 1-2 mm increments for L, W, H and 1-2 degrees for tapers). By way of example only, the implants of the present invention may be provided in lengths ranging from 35-65 mm, heights ranging from 6-18 mm, width ranging from 18-30 mm, lordotic tapers ranging from 0-12 degrees, and coronal tapers ranging from 0-15 degrees.

The individual base members and closure member may also be sized in any number of suitable manners, including: (a) for base members, lengths ranging from 30-50 mm, heights ranging from 6-18 mm, widths ranging from 18-30 mm, lordotic tapers ranging from 0-12 degrees, and coronal tapers ranging from 0-15 degrees, and (b) for the closure members, lengths ranging from 5-25 mm, heights ranging from 6-18 mm, widths ranging from 18-30 mm, lordotic tapers ranging from 0-12 degrees, and coronal tapers ranging from 0-15 degrees.

As noted above, any number of inserters can be used to implant the base members 12 and closure members 14 disclosed herein according to an aspect of the present invention, including those designs illustrated in FIGS. 25-37. This is evidenced, by way of example only, with reference to FIGS. 41-42, which show the distal end of an inserter 200 for use with the base member 12 of FIGS. 25-29. The inserter 200 is of the same general construction and configuration as the inserter 60 of FIGS. 7-9, except that the lateral members 74 of the insertion region 66 are dimensioned in a generally acutely angled manner to abut the generally angled trailing ends 76 of the side walls 16 when the main body 72 is positioned within the base member 12. In this manner, the insertion region 66 retains the trailing ends 76 of the side walls 16 by causing the trailing ends 76 to be disposed within the acute angle formed by the lateral members 74, thereby preventing any unwanted splay during introduction. Other than this distinction, the inserter 200 operates in the same manner as the inserter 60 such that the description need not be repeated.

Having described a multitude of aspects of the present invention, including aspects of the interbody fusion implant, the inserters for each member of the interbody fusion implant, and associated methodology, it should be understood that this invention is not limited to only those aspects described above and that changes and modifications may be made without departing from the true spirit and scope of the invention as defined in the appended claims.

What is claimed is:

1. An interbody fusion implant for use in lateral access spinal surgery, comprising:
    a base member having a first side wall, a second side wall and an end wall integrally coupled between respective first ends of the first side wall and the second side wall and spacing the side walls to define defining an open trailing end coinciding with second ends of the side walls located opposite the first ends thereof, and to define an interior bounded by the side walls and the end wall, at least a portion of the end wall dimensioned to serve as a structural support between cortical bone regions of adjacent vertebral bodies in the lumbar or thoracic spine, and the side walls and the end wall being dimensioned to serve as a protective barrier between the interior and adjacent neural structure and/or vasculature, the sidewalls and the end wall defining unobstructed areas on the adjacent vertebral bodies beginning from the open trailing end for end plate preparation after the base member is positioned between the adjacent vertebral bodies;
    a closure member configured for assembly onto the second ends of the side walls of the base member to enclose the interior after the base member has been positioned in a preliminarily prepared disc space in between the vertebral bodies and end plate preparation has taken place within the interior of the base member, the closure member being dimensioned to make contact with the vertebral bodies after it is locked to the base member to provide partial structural support between cortical bone regions of the adjacent vertebral bodies and including first and second overlapping portions each located adjacent a respective end of the closure member and each extending over a respective second end of a side wall when said closure member and said base member are assembled;
    a first elongated tie and a second elongated tie, each elongated tie having a first embedded portion terminating at a first terminal end thereof and a second projecting portion that includes a second terminal end thereof located opposite the first terminal end, each first embedded portion being either received in and affixed to one of the side walls with its projecting away from a respective second end, or received in and affixed to the closure member with its projecting portion projecting from a respective overlapping portion, the projecting portion including an end portion, which includes the second terminal end, the end portion being no wider than the rest of the projecting portion; and
    a first elongated bore and a second elongated bore, each bore being defined in either a respective side wall or defined in the closure member, each bore having a mouth defined at a respective second end of a side wall or at a respective overlapping portion dimensioned to receive a respective projecting portion, and each bore having an interior dimensioned to have at least a portion of an interior surface thereof frictionally engage a respective projecting portion of a respective elongated tie, wherein the bores register with the projecting portions to allow the closure member and the side walls to align with one another during assembly of the closure member onto the side walls of the base member.

2. The implant of claim 1, wherein the first elongated tie and the second elongated tie are pins.

3. The implant of claim 1, wherein the closure member includes a portion that abuts the sidewalls and a portion that is receivable in the interior of the base member from the open trailing end.

4. The implant of claim 1, wherein the elongated ties are comprised of a radiopaque material and the base member and the closure member are comprised of a radiolucent material.

5. The implant of claim 4, wherein the elongated ties are metallic.

6. The implant of claim 5, wherein the radiolucent material is PEEK.

7. An interbody fusion implant system for lateral access spinal surgery, comprising:
    a base member having a first side wall, a second side wall and an end wall integrally coupled between respective first ends of the first side wall and the second side wall and spacing the side walls to define an open trailing end coinciding with second ends of the side walls located opposite the first ends thereof, and to define an interior bounded by the side walls and the end wall, at least a portion of the end wall dimensioned to serve as a structural support between cortical bone regions of adjacent vertebral bodies in the lumbar or thoracic spine, and the side walls and the end wall dimensioned to serve as a protective barrier between the interior and adjacent neural structure and/or vasculature, the sidewalls and the end wall defining unobstructed areas on the adjacent vertebral bodies beginning from the open trailing end for end plate preparation after the base member is positioned between the adjacent vertebral bodies;
    a closure member configured for assembly onto the second ends of the side walls of the base member to enclose the interior after the base member has been positioned in a preliminarily prepared disc space in between the adjacent vertebral bodies and final end plate preparation has taken place within the interior of the base member, the closure member being dimensioned to make contact with the vertebral bodies after it is locked to said base member whereby the closure member and the base member together provide structural support between cortical bone regions of the adjacent vertebral bodies, the closure member including first and second overlapping portions each located adjacent a respective end of the closure member and each extending over a respective second end of a side wall when said closure member and said base member are assembled;

a first elongated tie and a second elongated tie, each elongated tie having a first embedded portion that includes a first terminal end thereof and a second projecting portion that includes a second terminal end thereof located opposite the first terminal end, each first embedded portion being either embedded in and affixed to one of the side walls with its projecting portion projecting away from a respective second end, or embedded in and affixed to the closure member with its projecting portion projecting from a respective overlapping portion the projecting portion including an end portion, which includes the second terminal end, and is no wider than the rest of the projecting portion; and a first elongated bore and a second elongated bore, each bore being defined in either a respective side wall or defined in the closure member, each bore having a mouth defined at a respective second end of a side wall or at a respective overlapping portion dimensioned to receive a respective projecting portion, and each bore having an interior dimensioned to have at least a portion of an interior surface thereof frictionally engage a respective projecting portion of a respective elongated tie, wherein the bores register with the projecting portions to allow the closure member and the side walls to align with one another during assembly of the closure member onto the side walls of the base member.

8. The system of claim 7, wherein the first elongated tie and the second elongated tie are pins.

9. The implant of claim 7, wherein the closure member includes alignment features projecting from a surface thereof and dimensioned to be received by the base member to align the closure member and the base member.

\* \* \* \* \*